United States Patent
Shibayama et al.

(10) Patent No.: US 12,384,749 B2
(45) Date of Patent: Aug. 12, 2025

(54) ONIUM SALT OF NITROGEN-CONTAINING HETEROARYL COMPOUND AND PEST CONTROL AGENT

(71) Applicant: Nippon Soda Co., Ltd., Tokyo (JP)

(72) Inventors: Kotaro Shibayama, Odawara (JP); Hiroto Suzuki, Odawara (JP); Riho Taguchi, Odawara (JP); Takao Iwasa, Odawara (JP); Kento Iwata, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 719 days.

(21) Appl. No.: 17/641,056

(22) PCT Filed: Sep. 9, 2020

(86) PCT No.: PCT/JP2020/034092
§ 371 (c)(1),
(2) Date: Mar. 7, 2022

(87) PCT Pub. No.: WO2021/049522
PCT Pub. Date: Mar. 18, 2021

(65) Prior Publication Data
US 2022/0332686 A1 Oct. 20, 2022

(30) Foreign Application Priority Data

Sep. 12, 2019 (JP) ................. 2019-166676

(51) Int. Cl.
| | | |
|---|---|---|
| C07D 237/08 | (2006.01) |
| A01N 43/50 | (2006.01) |
| A01N 43/56 | (2006.01) |
| A01N 43/58 | (2006.01) |
| A01N 43/60 | (2006.01) |
| A01N 43/653 | (2006.01) |
| A01N 43/78 | (2006.01) |
| A01N 43/80 | (2006.01) |
| C07D 231/12 | (2006.01) |

(Continued)

(52) U.S. Cl.
CPC .......... *C07D 237/08* (2013.01); *A01N 43/50* (2013.01); *A01N 43/56* (2013.01); *A01N 43/58* (2013.01); *A01N 43/60* (2013.01); *A01N 43/653* (2013.01); *A01N 43/78* (2013.01); *A01N 43/80* (2013.01); *C07D 231/12* (2013.01); *C07D 233/56* (2013.01); *C07D 235/22* (2013.01); *C07D 241/12* (2013.01); *C07D 249/08* (2013.01); *C07D 277/22* (2013.01); *C07D 277/60* (2013.01); *C07D 401/12* (2013.01); *C07D 403/12* (2013.01)

(58) Field of Classification Search
CPC .. C07D 237/08; C07D 231/12; C07D 233/56; C07D 235/22; C07D 241/12; C07D 249/08; C07D 277/22; C07D 277/60; C07D 401/12; C07D 403/12; A01N 43/50; A01N 43/56; A01N 43/58; A01N 43/60; A01N 43/653; A01N 43/78; A01N 43/80
See application file for complete search history.

(56) References Cited

U.S. PATENT DOCUMENTS

| | | | |
|---|---|---|---|
| 3,886,171 A | 5/1975 | Parsons |
| 4,602,944 A | 7/1986 | West |
| 2020/0275655 A1 | 9/2020 | Iwasa et al. |

FOREIGN PATENT DOCUMENTS

| | | | |
|---|---|---|---|
| DE | 289269 A5 * | 4/1991 |
| JP | 60-104068 A | 6/1985 |

(Continued)

OTHER PUBLICATIONS

Nagasawa et al., Photoreaction of Heteroaromatic N-Imines with poly(vinyl alcohol) Journal of Photopolymer Science and Technology, 1996, vol. 9, No. 1, pp. 93, 94. (Year: 1996).*

(Continued)

*Primary Examiner* — Blessing M Fubara
(74) *Attorney, Agent, or Firm* — FITCH, EVEN, TABIN & FLANNERY LLP

(57) ABSTRACT

A compound represented by formula (I) or formula (II) has a pest control effect. (In the formulae, $Q^1$ represents a pyrazine ring or the like; $G^1$ represents a nitrogen atom or a carbon atom; $X^1$ represents an alkyl group or the like; m represents the number of $X^1$ moieties; A represents an oxygen atom or the like; Y represents a single bond or the like; $Q^2$ represents a benzene ring or the like; $X^2$ represents an alkyl group, an aryl group or the like; $X^3$ represents a halogeno group or the like; n represents the number of $X^3$ moieties; $Z^{q-}$ represents a counter ion; and q represents 1 or 2.)

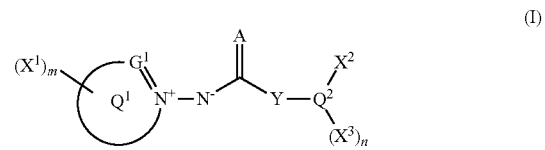

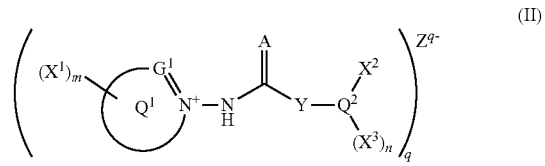

10 Claims, No Drawings

(51) Int. Cl.
  *C07D 233/56* (2006.01)
  *C07D 235/22* (2006.01)
  *C07D 241/12* (2006.01)
  *C07D 249/08* (2006.01)
  *C07D 277/22* (2006.01)
  *C07D 277/60* (2006.01)
  *C07D 401/12* (2006.01)
  *C07D 403/12* (2006.01)

(56) References Cited

FOREIGN PATENT DOCUMENTS

| JP | 04-267251 A | 9/1992 |
| JP | 04-319947 A | 11/1992 |
| WO | WO-2019/107348 A1 | 6/2019 |

OTHER PUBLICATIONS

Costello et al., "Selective deprotection of phthalyl protected amines," Tetrahedron Letters, Jan. 6, 1997, 38(1):1.

Kwak et al., "N-Aminopyridinium Ylide-Directed, Copper-Promoted Amination of sp2 C—H Bonds,", The Journal of Organic Chemistry, Sep. 10, 2019, 84(20):13022-13032.

Schulze et al., "Synthesis of novel N-aroyl- and N-arylsulfonylisothiazole-2-imines by cyclization of thiocyanatovinyl aldehyde hydrazones," Tetrahedron Letters, Jan. 1, 1993, 34(12):1909-1912.

Supplementary European Search Report dated Sep. 14, 2023 in EP 20863312.3.

Wang et al., "Synthesis of Heterocyclic Ylids as Candidates for Energetic Materials," Journal of Energetic Materials, Apr. 8, 2014, 32(4):227-237.

CAS Registry No. 1265907-92-3, retrieved on Oct. 26, 2020 from STN, 1 page.

CAS Registry No. 1266249-37-9, retrieved on Oct. 26, 2020 from STN, 1 page.

Guernon et al., "N-Acyliminoimidazolium Ylides as Precursors to Anionic N-Heterocyclic Carbene Ligands: Control of Topology and Reactivity," Organometallics, Mar. 11, 2013, 32:1988-1994.

International Search Report dated Nov. 10, 2020 in PCT/JP2020/034092, with English translation.

Kamata et al., "Synthesis and Photolysis of a Series of Substituted Aroyl Nitrogen Ylides: Development of Photo-Cross-Linking and Photolabeling Reagents," J. Org. Chem., 1993, 58:5323-5328.

Kolberg et al., "Oxidation of Acceptor-substituted Isothiazolium-2-imines to Stable Cyclic Sulfin- and Sulfonamides with 3-Hydroperoxy Function," J. Prakt. Chem., 2000, 3:291-296.

Nagasawa et al., "Photoreaction of heteroaromatic N-imines with poly(vinyl alcohol)," Journal of Photopolymer Science and Technology, 1996, 9(1):93-94.

Nagasawa et al., "Photoreaction of poly(vinyl alcohol) having N-(1-methyl-4-(1,2,4-triazolio))benzamidate," Journal of Photopolymer Science and Technology, 1995, 8(1):119-124.

Schantl, J.G., "Product Class 19: Azomethine Imines," Science of Synthesis, 2004, 27:731-824.

Schmidt et al., "Isothiazolo[3,2, b]-1,3,4-oxadiazole-5,5-dioxide: Synthesis of a new heteropentalene system," Heterocycles, 2005, 65(11):2705-2720.

Schulze et al., "Synthese neuer N-Aroylisothiazol-2-imine und N-Aroylamino-isothiazoliumsalze durch Cyclisierung von thiocyanato-substituierten Hydrazonen," J. Prakt. Chem., 1994, 336:115-120.

Zhang et al., "The synthesis and energetic properties of pyridinium and triazolium N-(nitrobenzoyl)-imides," ARKIVOC, 2016, 3:99-109.

\* cited by examiner

ONIUM SALT OF NITROGEN-CONTAINING HETEROARYL COMPOUND AND PEST CONTROL AGENT

TECHNICAL FIELD

The present invention relates to an onium salt of a nitrogen-containing heteroaryl compound and a pest control agent. In more detail, the present invention relates to an onium salt of a nitrogen-containing heteroaryl compound that has excellent insecticidal activity and/or acaricidal activity, and excellent safety, and that can be synthesized industrially advantageously, as well as a pest control agent containing the same as an active ingredient thereof.

The present invention claims priority on the basis of Japanese Patent Application No. 2019-166676 filed in Japan on Sep. 12, 2019, the contents of which are incorporated herein by reference.

BACKGROUND OF THE INVENTION

Various compounds having insecticidal and/or acaricidal activity have been proposed. In the case where such compounds are used as agrochemicals, the compounds are required not only to exhibit high efficacy, but also to exhibit less possibility of causing chemical resistance, harmful effects on plants, or soil pollution, and to exhibit low toxicity to domestic animals or fish.

Patent Document 1 discloses a pyridinium salt of formula (A) which exhibits pest control effects.

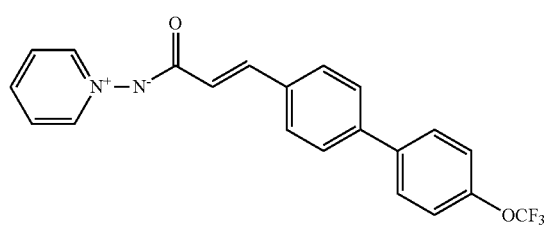

(A)

DOCUMENTS OF RELATED ART

Patent Documents

Patent Document 1: WO 2019/107348 A1

SUMMARY OF THE INVENTION

Problems to be Solved by the Invention

An object of the present invention is to provide an onium salt of a nitrogen-containing heteroaryl compound (hereinafter, may be abbreviated as "aromacyclic quaternary ammonium compound") that has excellent pest control activity, particularly insecticidal activity and/or acaricidal activity, and excellent safety, and that can be synthesized industrially advantageously. Another object of the present invention is to provide a pest control agent, insecticide, acaricide, ectoparasite control agent, endoparasite control agent, or expellant, containing the aromacyclic quaternary ammonium compound as an active ingredient thereof.

Means to Solve the Problems

The present invention encompassing the following aspects has been completed as a result of studying to solve the above-described problems.

(1) A compound of formula (I) or formula (II).

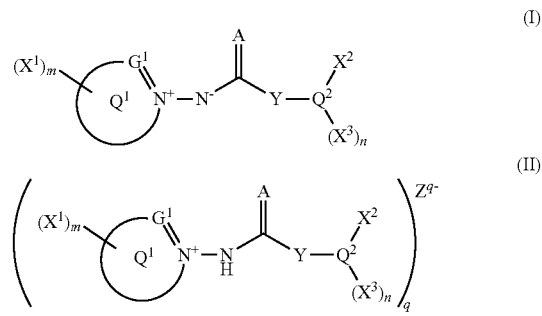

In the formulae (I) and (II), $Q^1$ is a pyrazole ring, an imidazole ring, a 1,2,4-triazole ring, an oxazole ring, a thiazole ring, an isoxazole ring, an isothiazole ring, a pyrazine ring, a pyrimidine ring, or a pyridazine ring, $G^1$ is a nitrogen atom or a carbon atom, $X^1$ is a halogeno group, a substituted or unsubstituted C1-6 alkyl group, a substituted or unsubstituted C2-6 alkenyl group, a substituted or unsubstituted C2-6 alkynyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- or 6-membered heteroaryl group, a pentafluorosulfanyl group, a nitro group, or a cyano group, m indicates the number of $X^1$, and m is an integer of 1 to 3 when $Q^1$ is a pyrazole ring, an imidazole ring, or a 1,2,4-triazole ring, and is an integer of 0 to 3 when $Q^1$ is an oxazole ring, a thiazole ring, an isoxazole ring, an isothiazole ring, a pyrazine ring, a pyrimidine ring, or a pyridazine ring, $X^1$ on adjacent carbon atoms may form together a cyclohexene ring including these two carbon atoms, A is an oxygen atom or a sulfur atom, Y is a single bond, or a substituted or unsubstituted C2-6 alkenylene group, $Q^2$ is a benzene ring, a naphthalene ring, or a 5- to 10-membered heteroaryl ring, $X^2$ is a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C3-8 cycloalkyloxy group, a substituted or unsubstituted C6-10 aryl group, a substituted or unsubstituted C6-10 aryloxy group, a substituted or unsubstituted 5- or 6-membered heteroaryl group, a substituted or unsubstituted 5- or 6-membered heteroaryloxy group, a formyl group, a group of R—CO—, a group of RO—CO—, an amino group, a group of RNH—, a group of R$_2$N—, a group of RCONH—, a group of RO—CONH—, a carbamoyl group, a group of RNH—CO—, a group of R$_2$N—CO—, a group of RO—N=CH—, a pentafluorosulfanyl group, a nitro group, or a cyano group, R is each independently a substituted or unsubstituted C1-6 alkyl group, a substituted or unsubstituted C6-10 aryl group, or a substituted or unsubstituted 5- or 6-membered heteroaryl group, X$^3$ is a halogeno group, a substituted or unsubstituted C1-6 alkyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a nitro group, or a cyano group, n indicates the number of X$^3$, and n is an integer of 0 to 4 when Q$^2$ is a benzene ring, and is an integer of 0 to 3 when Q$^2$ is a 5- or 6-membered heteroaryl ring, X$^2$ and X$^3$ on adjacent carbon atoms may form together a substituted or unsubstituted 5-membered hetero ring including these two carbon atoms, Z$^{q-}$ is a counter ion, and q indicates a valence of the counter ion and is 1 or 2.

(2) A pest control agent containing at least one selected from the compounds of (1) as an active ingredient thereof.

(3) An insecticide or acaricide containing at least one selected from the compounds of (1) as an active ingredient thereof.

(4) An ectoparasite control agent containing at least one selected from the compounds of (1) as an active ingredient thereof.

(5) An endoparasite control agent or expellant containing at least one selected from the compounds of (1) as an active ingredient thereof.

Effects of the Invention

The aromacyclic quaternary ammonium compound of the present invention has control activity against pests that cause problems to agricultural crops or in the health field. The control agent containing the aromacyclic quaternary ammonium compound of the present invention can effectively control pests, particularly agricultural insect pests and acarians, at lower doses, and can further effectively control ectoparasites and endoparasites that may harm humans and animals.

EMBODIMENTS FOR CARRYING OUT THE INVENTION

An aromacyclic quaternary ammonium compound of the present invention is a compound of formula (I) (inner salt) or a compound of formula (II) (intermolecular salt). The inner salt is a compound having both a cation center and an anion center in one molecule that is a zwitterion. The intermolecular salt is a compound formed by ionic association between a cation and anion that form an ionic pair.

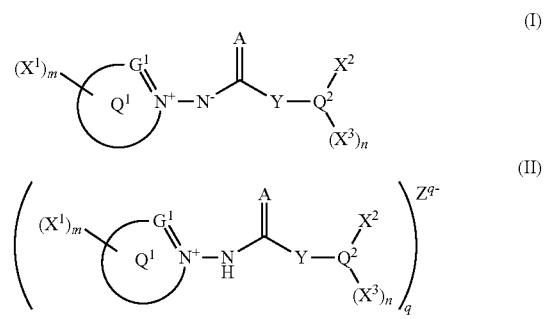

The term "unsubstituted" refers to a group consisting of a mother nucleus. In the case where only the name of a group serving as a mother nucleus is provided without accompanying the term "substituted", this refers to "unsubstituted" unless specifically indicated otherwise.

On the other hand, the term "substituted" means that any hydrogen atom of a group serving as a mother nucleus is substituted with a group (substituent) having a structure that is identical to or different from the mother nucleus. Thus, a "substituent" is another group bound to a group serving as the mother nucleus. The number of substituents may be one or two or more. Two or more substituents may be identical to or different from each other.

The term "C1-6", for example, indicates that the number of carbon atoms of the group serving as the mother nucleus is 1 to 6. The number of carbon atoms does not include the number of carbon atoms present in substituents. For example, a butyl group having an ethoxy group as a substituent thereof is classified as a C2 alkoxy C4 alkyl group.

There are no particular limitations on "substituents" provided that they are chemically available and achieve the effects of the present invention. Specific examples of groups that can be "substituents" include the following groups:

C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group;

C2-6 alkenyl groups such as a vinyl group, a 1-propenyl group, a 2-propenyl group (an allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-8 cycloalkyl groups such as a cyclopropyl group, a cyclobutyl group, a cyclopentyl group, a cyclohexyl group, and a cubanyl group;

C6-10 aryl groups such as a phenyl group and a naphthyl group;

C6-10 aryl C1-6 alkyl groups such as a benzyl group and a phenethyl group;

3- to 6-membered heterocyclyl groups;

3- to 6-membered heterocyclyl C1-6 alkyl groups;

a hydroxy group;

C1-6 alkoxy groups such as a methoxy group, an ethoxy group, a n-propoxy group, an i-propoxy group, a n-butoxy group, a s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group, and a propargyloxy group;
C6-10 aryloxy groups such as a phenoxy group, and a naphthoxy group;
C6-10 aryl C1-6 alkoxy groups such as a benzyloxy group, and a phenethyloxy group;
5- or 6-membered heteroaryloxy groups such as a thiazolyloxy group, and a pyridyloxy group;
5- or 6-membered heteroaryl C1-6 alkyloxy groups such as a thiazolylmethyloxy group, and a pyridylmethyloxy group;
a formyl group;
C1-6 alkylcarbonyl groups such as an acetyl group, and a propionyl group;
a formyloxy group;
C1-6 alkylcarbonyloxy groups such as an acetyloxy group, and a propionyloxy group;
C6-10 arylcarbonyl groups such as a benzoyl group;
C1-6 alkoxycarbonyl groups such as a methoxycarbonyl group, an ethoxycarbonyl group, a n-propoxycarbonyl group, an i-propoxycarbonyl group, a n-butoxycarbonyl group, and a t-butoxycarbonyl group;
C1-6 alkoxycarbonyloxy groups such as a methoxycarbonyloxy group, an ethoxycarbonyloxy group, a n-propoxycarbonyloxy group, an i-propoxycarbonyloxy group, a n-butoxycarbonyloxy group, and a t-butoxycarbonyloxy group;
a carboxyl group;
halogeno groups such as a fluoro group, a chloro group, a bromo group, and an iodo group;
C1-6 haloalkyl groups such as a chloromethyl group, a chloroethyl group, a trifluoromethyl group, a 1,2-dichloro-n-propyl group, and a 1-fluoro-n-butyl group;
C2-6 haloalkenyl groups such as a 2-chloro-1-propenyl group, and a 2-fluoro-1-butenyl group;
C2-6 haloalkynyl groups such as a 4,4-dichloro-1-butynyl group, a 4-fluoro-1-pentynyl group, and a 5-bromo-2-pentynyl group;
C1-6 haloalkoxy groups such as a trifluoromethoxy group, a 2-chloro-n-propoxy group, and a 2,3-dichlorobutoxy group;
C2-6 haloalkenyloxy groups such as a 2-chloropropenyloxy group, and a 3-bromobutenyloxy group;
C1-6 haloalkylcarbonyl groups such as a chloroacetyl group, a trifluoroacetyl group, and a trichloroacetyl group;
an amino group;
C1-6 alkyl-substituted amino groups such as a methylamino group, a dimethylamino group, and a diethylamino group;
C6-10 arylamino groups such as an anilino group, and a naphthylamino group;
C6-10 aryl C1-6 alkylamino groups such as a benzylamino group, and a phenethylamino group;
a formylamino group;
C1-6 alkylcarbonylamino groups such as an acetylamino group, a propanoylamino group, a butyrylamino group, and an i-propylcarbonylamino group;
C1-6 alkoxycarbonylamino groups such as a methoxycarbonylamino group, an ethoxycarbonylamino group, a n-propoxycarbonylamino group, and an i-propoxycarbonylamino group;
unsubstituted or substituted aminocarbonyl groups such as a carbamoyl group, a dimethylaminocarbonyl group, a phenylaminocarbonyl group, and a N-phenyl-N-methylaminocarbonyl group;
imino C1-6 alkyl groups such as an iminomethyl group, a (1-imino)ethyl group, and a (1-imino)-n-propyl group;
substituted or unsubstituted N-hydroxyimino C1-6 alkyl groups such as a N-hydroxy-iminomethyl group, a (1-(N-hydroxy)-imino)ethyl group, a (1-(N-hydroxy)-imino)propyl group, a N-methoxy-iminomethyl group, and a (1-(N-methoxy)-imino)ethyl group;
an aminocarbonyloxy group;
C1-6 alkyl-substituted aminocarbonyloxy groups such as an ethylaminocarbonyloxy group, and a dimethylaminocarbonyloxy group;
a mercapto group;
C1-6 alkylthio groups such as a methylthio group, an ethylthio group, a n-propylthio group, an i-propylthio group, a n-butylthio group, an i-butylthio group, a s-butylthio group, and a t-butylthio group;
C1-6 haloalkylthio groups such as a trifluoromethylthio group, and a 2,2,2-trifluoroethylthio group;
C6-10 arylthio groups such as a phenylthio group, and a naphthylthio group;
5- or 6-membered heteroarylthio groups such as a thiazolylthio group, and a pyridylthio group;
C1-6 alkylsulfinyl groups such as a methylsulfinyl group, an ethylsulfinyl group, and a t-butylsulfinyl group;
C1-6 haloalkylsulfinyl groups such as a trifluoromethylsulfinyl group, and a 2,2,2-trifluoroethylsulfinyl group;
C6-10 arylsulfinyl groups such as a phenylsulfinyl group;
5- or 6-membered heteroarylsulfinyl groups such as a thiazolylsulfinyl group, and a pyridylsulfinyl group;
C1-6 alkylsulfonyl groups such as a methylsulfonyl group, an ethylsulfonyl group, and a t-butylsulfonyl group;
C1-6 haloalkylsulfonyl groups such as a trifluoromethylsulfonyl group, and a 2,2,2-trifluoroethylsulfonyl group;
C6-10 arylsulfonyl groups such as a phenylsulfonyl group;
5- or 6-membered heteroarylsulfonyl groups such as a thiazolylsulfonyl group, and a pyridylsulfonyl group;
C1-6 alkylsulfonyloxy groups such as a methylsulfonyloxy group, an ethylsulfonyloxy group, and a t-butylsulfonyloxy group;
C1-6 haloalkylsulfonyloxy groups such as a trifluoromethylsulfonyloxy group, and a 2,2,2-trifluoroethylsulfonyloxy group;
tri C1-6 alkyl-substituted silyl groups such as a trimethylsilyl group, a triethylsilyl group, and a t-butyldimethylsilyl group;
tri C6-10 aryl-substituted silyl groups such as a triphenylsilyl group;
a pentafluorosulfanyl group;
a cyano group; and a nitro group.

Any hydrogen atom of the "substituent" may be substituted with a group having a different structure. Examples of such a substituent include C1-6 alkyl groups, C1-6 haloalkyl groups, C1-6 alkoxy groups, C1-6 haloalkoxy groups, halogeno groups, a cyano group, and a nitro group.

The "3- to 6-membered heterocyclyl group" is a 3-membered ring, a 4-membered ring, a 5-membered ring or a 6-membered ring which contains, as a ring member atom, one to four hetero atoms selected from the group consisting of a nitrogen atom, an oxygen atom and a sulfur atom. The heterocyclyl group may be monocyclic or polycyclic. If at least one ring of a polycyclic heterocyclyl group is a hetero ring, the remaining rings thereof may be any of saturated alicyclic rings, unsaturated alicyclic rings and aromatic rings. Examples of the "3- to 6-membered heterocyclyl group" include 3- to 6-membered saturated heterocyclyl groups, 5- or 6-membered heteroaryl groups, and 5- or 6-membered partially unsaturated heterocyclyl groups.

Examples of the 3- to 6-membered saturated heterocyclyl groups include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

($Z^{q-}$)

In the formula (II), $Z^{q-}$ is a counter ion, and q indicates a valence of the counter ion and is 1 or 2. Specific examples of a monovalent anion $Z^-$ include $Cl^-$, $Br^-$, $I^-$, $NO_3^-$, $CH_3COO^-$, $CH_3SO_3^-$, $CF_3SO_3^-$, and $TolSO_3^-$. Specific examples of a divalent anion $Z^{2-}$ include $SO_4^{2-}$. Tol is an abbreviation which refers to an o-methylphenyl group, m-methylphenyl group or a p-methylphenyl group.

In the present invention, $Z^{q-}$ is preferably a monovalent anion $Z^-$, and specifically preferably $Cl^-$, $Br^-$, or $I^-$.

($Q^1$)

In the formulae (I) and (II), $Q^1$ is a pyrazole ring, an imidazole ring, a 1,2,4-triazole ring, an oxazole ring, a thiazole ring, an isoxazole ring, an isothiazole ring, a pyrazine ring, a pyrimidine ring, or a pyridazine ring, and $G^1$ is a nitrogen atom or a carbon atom.

($X^1$, m)

In the formulae (I) and (II), $X^1$ is a halogeno group, a substituted or unsubstituted C1-6 alkyl group, a substituted or unsubstituted C2-6 alkenyl group, a substituted or unsubstituted C2-6 alkynyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- or 6-membered heteroaryl group, a pentafluorosulfanyl group, a nitro group, or a cyano group.

m indicates the number of $X^1$, and is an integer of 1 to 3 when $Q^1$ is a pyrazole ring, an imidazole ring, or a 1,2,4-triazole ring, and is an integer of 0 to 3 when $Q^1$ is an oxazole ring, a thiazole ring, an isoxazole ring, an isothiazole ring, a pyrazine ring, a pyrimidine ring, or a pyridazine ring. In the case where m is 2 or more, $X^1$ may be identical to or different from each other.

$X^1$ on adjacent carbon atoms may form together a cyclohexene ring including these two carbon atoms Examples of the "halogeno group" as $X^1$ include a fluoro group, a chloro group, a bromo group, and an iodo group.

The "C1-6 alkyl group" as $X^1$ may be a linear chain or a branched chain. Examples of the "C1-6 alkyl group" as $X^1$ include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" as $X^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Examples of the "C2-6 alkynyl group" as $X^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C1-6 alkoxy group" as $X^1$ include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the "C1-6 alkylthio group" as $X^1$ include a methylthio group, an ethylthio group, a n-propylthio group, a n-butylthio group, a n-pentylthio group, a n-hexylthio group, and an i-propylthio group.

Examples of the "C1-6 alkylsulfinyl group" as $X^1$ include a methylsulfinyl group, an ethylsulfinyl group, and a t-butylsulfinyl group.

Examples of the "C1-6 alkylsulfonyl group" as $X^1$ include a methylsulfonyl group, an ethylsulfonyl group, and a t-butylsulfonyl group.

Preferable examples of a substituent on the "C1-6 alkyl group", "C2-6 alkenyl group", "C2-6 alkynyl group", "C1-6 alkoxy group", "C1-6 alkylthio group", "C1-6 alkylsulfinyl group", or "C1-6 alkylsulfonyl group" as $X^1$ include: halogeno groups such as a fluoro group, a chloro group, a bromo group, and an iodo group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; C6-10 aryl groups such as a phenyl group, and a naphthyl group; C6-10 aryl groups substituted with a halogeno group, a C1-6 haloalkyl group, or a C1-6 haloalkoxy group, such as a 4-chlorophenyl group, a 4-trifluoromethylphenyl group, and a 4-trifluoromethoxyphenyl group; and a cyano group.

Examples of the "C3-8 cycloalkyl group" as $X^1$ include a cyclopropyl group, a cyclobutyl group, a cyclopentyl group, a cyclohexyl group, and a cycloheptyl group.

Examples of the "C6-10 aryl group" as $X^1$ include a phenyl group, and a naphthyl group.

The "5- or 6-membered heteroaryl group" as $X^1$ is a 5-membered ring or a 6-membered ring which contains, as a ring member atom, one, two, three, or four hetero atoms selected from the group consisting of a nitrogen atom, an oxygen atom and a sulfur atom. In the case where at least two hetero atoms are present, the hetero atoms may be identical to or different from each other.

Examples of the 5-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

Preferable examples of a substituent on the "C3-8 cycloalkyl group", "C6-10 aryl group", or "5- or 6-membered heteroaryl group" as $X^1$ include: halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; and a cyano group.

In the present invention, $X^1$ is preferably a halogeno group; a phenyl-substituted, halogeno-substituted, or unsubstituted C1-6 alkyl group; or a halogeno-substituted, or unsubstituted C1-6 alkoxy group, and more preferably a halogeno-substituted or unsubstituted C1-6 alkyl group.

Examples of the "phenyl-substituted C1-6 alkyl group" as $X^1$ include a benzyl group, and a phenethyl group.

Examples of the "halogeno-substituted C1-6 alkyl group" as $X^1$ include a difluoromethyl group, a trifluoromethyl group, a 2,2,2-trifluoroethyl group, and a 2,2,2,1,1-pentafluoroethyl group.

Examples of the "halogeno-substituted C1-6 alkoxy group" as $X^1$ include a difluoromethoxy group, a trifluoromethoxy group, a 2,2-difluoroethoxy group, a 2,2,2-trifluoroethoxy group, a 2,2,1,1-tetrafluoroethoxy group, and a 2,2,2,1,1-pentafluoroethoxy group.

Specific examples of the structure including $Q^1$ and $X^1$ (aromacyclic quaternary ammonium cation) are shown below. The symbol "-*" in the structure indicates a bond with "N⁻" in formula (I) and a bond with "NH" in formula (II).

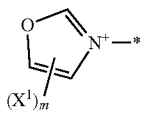
$Q^1$-1

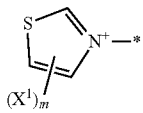
$Q^1$-2

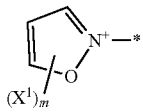
$Q^1$-3

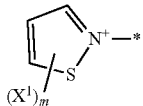
$Q^1$-4

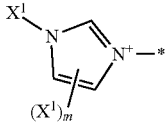
$Q^1$-5

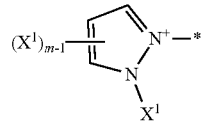
$Q^1$-6

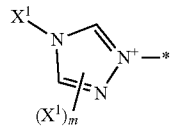
$Q^1$-7

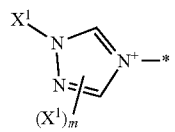
$Q^1$-8

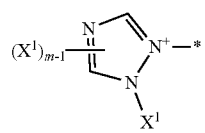
$Q^1$-9

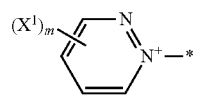
$Q^1$-10

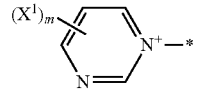
$Q^1$-11

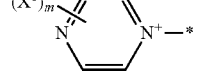
$Q^1$-12

In the present invention, the structure including $Q^1$ and $X^1$ is preferably $Q^1$-2, $Q^1$-5, $Q^1$-8, $Q^1$-10 or $Q^1$-12, and more preferably $Q^1$-5, $Q^1$-8, or $Q^1$-10, among the structures specifically shown above.

(A)

In the formulae (I) and (II), A is an oxygen atom or a sulfur atom.

In the present invention, A is preferably an oxygen atom.

(Y)

Y is a single bond, or a substituted or unsubstituted C2-6 alkenylene group.

Preferable examples of a substituent on the "C2-6 alkenylene group" as Y include: halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, and a t-butyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; C1-6 alkoxy C1-6 alkyl groups such as a methoxymethyl group; C1-6 alkylthio groups such as a methylthio group, an ethylthio group, a n-propylthio group, a i-propylthio group, a n-butylthio group, an i-butylthio group, a s-butylthio group, and a t-butylthio group; C1-6 alkylsulfinyl groups such as a methylsulfinyl group, an ethylsulfinyl group, and a t-butylsulfinyl group; and C1-6 alkylsulfonyl groups such as a methylsulfonyl group, an ethylsulfonyl group, and a t-butylsulfonyl group.

In the present invention, Y is preferably a single bond; or a substituted (halogeno-substituted or C1-6 alkyl-substituted), or unsubstituted C2-6 alkenylene group.

($Q^2$)

$Q^2$ is a benzene ring, a naphthalene ring, or a 5- to 10-membered heteroaryl ring.

The "5- to 10-membered heteroaryl ring" is a 5- to 10-membered aromatic ring which contains, as a ring member atom, 1 to 4 hetero atoms selected from the group consisting of a nitrogen atom, an oxygen atom and a sulfur atom. The heteroaryl ring may be monocyclic or polycyclic.

Examples of the 5-membered heteroaryl ring include a pyrrol ring, a furan ring, a thiophen ring, an imidazole ring, a pyrazole ring, an oxazole ring, an isoxazole ring, a thiazole ring, an isothiazole ring, a triazole ring, an oxadiazole ring, a thiadiazole ring, and a tetrazole ring.

Examples of the 6-membered heteroaryl ring include a pyridine ring, a pyrazine ring, a pyrimidine ring, a pyridazine ring, and a triazine ring.

Examples of the 9-membered heteroaryl ring include an indole ring, an isoindole ring, a benzofuran ring, a benzothiophen ring, an indazole ring, a benzoimidazole ring, a benzoxazole ring, a benzisoxazole ring, a benzothiazole ring, and a benzoisothiazole ring.

Examples of the 10-membered heteroaryl ring include a quinoline ring, an isoquinoline ring, a quinazoline ring, and a quinoxaline ring.

In the present invention, $Q^2$ is preferably a benzene ring, a naphthalene ring, a pyridine ring, a pyrimidine ring, or a benzothiazole ring, and more preferably a benzene ring or a pyridine ring.

($X^2$, R)

$X^2$ is a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C3-8 cycloalkyloxy group, a substituted or unsubstituted C6-10 aryl group, a substituted or unsubstituted C6-10 aryloxy group, a substituted or unsubstituted 5- or 6-membered heteroaryl group, a substituted or unsubstituted 5- or 6-membered heteroaryloxy group, a formyl group, a group of R—CO—, a group of RO—CO—, an amino group, a group of RNH—, a group of $R_2$N—, a group of RCONH—, a group of RO—CONH—, a carbamoyl group, a group of RNH—CO—, a group of $R_2$N—CO—, a group of RO—N=CH—, a pentafluorosulfanyl group, a nitro group, or a cyano group.

Specific examples of the halogeno group, the substituted or unsubstituted C1-6 alkyl group, the substituted or unsubstituted C2-6 alkenyl group, the substituted or unsubstituted C2-6 alkynyl group, the hydroxy group, the substituted or unsubstituted C1-6 alkoxy group, the substituted or unsubstituted C1-6 alkylthio group, the substituted or unsubstituted C1-6 alkylsulfinyl group, the substituted or unsubstituted C1-6 alkylsulfonyl group, the substituted or unsubstituted C3-8 cycloalkyl group, the substituted or unsubstituted C6-10 aryl group, and the substituted or unsubstituted 5- or 6-membered heteroaryl group as $X^2$ include the same groups as those mentioned for $X^1$.

Examples of the "C2-6 alkenyloxy group" as $X^2$ include a vinyloxy group, an allyloxy group, a propenyloxy group, and a butenyloxy group.

Examples of the "C2-6 alkynyloxy group" as $X^2$ include an ethynyloxy group, and a propargyloxy group.

Examples of the "C3-8 cycloalkyloxy group" as $X^2$ include a cyclopropyloxy group, a cyclobutyloxy group, a cyclopentyloxy group, a cyclohexyloxy group, and a cycloheptyloxy group.

Examples of the "C6-10 aryloxy group" as $X^2$ include a phenoxy group, and a naphthoxy group.

The "5- or 6-membered heteroaryloxy group" as $X^2$ has a structure in which a 5- or 6-membered heteroaryl group and an oxy group are bound. Specific examples thereof include a thiazolyloxy group and a pyridyloxy group.

Preferable examples of a substituent on the "C2-6 alkenyloxy group", "C2-6 alkynyloxy group", or "C3-8 cycloalkyloxy group" as $X^2$ include: halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; and a cyano group.

In the "group of R—CO—", "group of RO—CO—", "group of RNH—", "group of $R_2$N—", "group of RCONH—", "group of RO—CONH—", "group of RNH—CO—", "group of $R_2$N—CO—", or "group of RO—N=CH—" as $X^2$, R is each independently a substituted or unsubstituted C1-6 alkyl group, a substituted or unsubstituted C6-10 aryl group, or a substituted or unsubstituted 5- or 6-membered heteroaryl group.

The "C1-6 alkyl group" as R may be a linear chain or a branched chain. Examples of the "C1-6 alkyl group" as R include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group. Preferable examples of a substituent on the "C1-6 alkyl group" include halogeno groups such as a fluoro group, a chloro group, a bromo group, and an iodo group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; C6-10 aryl groups such as a phenyl group, and a naphthyl group; C6-10 aryl groups such as a phenyl group, and a naphthyl group; C6-10 aryl groups substituted with a halogeno group, a C1-6 haloalkyl group, or a C1-6 haloalkoxy group, such as a 4-chlorophenyl group, a 4-trifluoromethylphenyl group, and a 4-trifluoromethoxyphenyl group; and a cyano group.

Examples of the "C6-10 aryl group" as R include a phenyl group and naphthyl group.

The "5- or 6-membered heteroaryl group" as R is a 5-membered or 6-membered ring which contains, as (a) ring member atom(s), one, two, three or four hetero atom(s) selected from the group consisting of a nitrogen atom, an oxygen atom and a sulfur atom. In the case where at least two hetero atoms are contained, the hetero atoms may be identical to or different from each other.

Examples of the 5-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

Preferable examples of a substituent on the "C6-10 aryl group" or "5- or 6-membered heteroaryl group" as R include halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; and a cyano group.

In the present invention, $X^2$ is preferably a halogeno group, a substituted or unsubstituted C1-6 alkyl group, a substituted or unsubstituted C2-6 alkenyl group, a substituted or unsubstituted C1-6 alkoxy group, a substituted or unsubstituted C6-10 aryl group, a substituted or unsubstituted C6-10 aryloxy group, a substituted or unsubstituted 5- or 6-membered heteroaryl group, or a substituted or unsubstituted 5- or 6-membered heteroaryloxy group, and more preferably a halogeno group, a substituted or unsubstituted C1-6 alkyl group, a substituted or unsubstituted C2-6 alkenyl group, a substituted or unsubstituted C1-6 alkoxy group, a substituted or unsubstituted a phenyl group, a substituted or unsubstituted phenoxy group, a substituted or unsubstituted isoxazolyl group, or a substituted or unsubstituted pyridyl group.

Preferable examples of a substituent on the "C1-6 alkyl group", "C2-6 alkenyl group", or "C1-6 alkoxy group" as $X^2$ include: halogeno groups such as a fluoro group, a chloro group, a bromo group, and an iodo group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; C6-10 aryl groups such as a phenyl group, and a naphthyl group; C6-10 aryl groups substituted with a halogeno group, a C1-6 haloalkyl group, or a C1-6 haloalkoxy group, such as a 4-chlorophenyl group, a 4-trifluoromethylphenyl group, and a 4-trifluoromethoxyphenyl group; C6-10 aryloxy groups such as a phenoxy group; halogeno-substituted, C1-6 haloalkyl-substituted, or C1-6 haloalkoxy-substituted C6-10 aryloxy groups such as a 4-chlorophenoxy group, a 4-trifluoromethylphenoxy group, and a 4-trifluoromethoxyphenoxy group; and a cyano group, and more preferable examples thereof include halogeno groups and C1-6 haloalkoxy groups.

Preferable examples of a substituent on the "C6-10 aryl group", "C6-10 aryloxy group", "5- or 6-membered heteroaryl group", or "5- or 6-membered heteroaryloxy group" as $X^2$ include: halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; and a cyano group, and more preferable examples thereof include C1-6 haloalkyl groups and C1-6 haloalkoxy groups.

In the present invention, $X^2$ is also preferably a group of RO—CO—, a group of RCONH—, a group of RO—CONH—, or a group of RO—N═CH—.

R is preferably a substituted or unsubstituted C1-6 alkyl group, and more preferably a halogeno-substituted or unsubstituted C1-6 alkyl group.

($X^3$, n)

$X^3$ is a halogeno group, a substituted or unsubstituted C1-6 alkyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a nitro group, or a cyano group.

n indicates the number of $X^3$, and n is an integer of 0 to 4, preferably an integer of 0 to 2, when $Q^2$ is a benzene ring, and is an integer of 0 to 3, preferably 0 or 1, when $Q^2$ is a 5- or 6-membered heteroaryl ring. When n is 2 or more, $X^3$ may be identical to or different from each other.

Specific examples of these groups as $X^3$ include the same groups as those mentioned as $X^1$.

In the present invention, $X^3$ is preferably a halogeno group; a halogeno-substituted or unsubstituted C1-6 alkyl group; a halogeno-substituted or unsubstituted C1-6 alkoxy group; a nitro group; or a cyano group, and more preferably a halogeno group; an unsubstituted C1-6 alkyl group; or a cyano group.

$X^2$ and $X^3$ on adjacent carbon atoms may form together a substituted or unsubstituted 5-membered hetero ring including these two carbon atoms. The "5-membered hetero ring" is a 5-membered ring which contains, as (a) ring member atom(s), one, two, or three hetero atom(s) selected from the group consisting of a nitrogen atom, an oxygen atom and a sulfur atom. In the case where at least two hetero atoms are contained, the hetero atoms may be identical to or different from each other.

Specific examples thereof include: partially unsaturated oxygen-containing hetero rings such as a 2,3-dihydrofuran ring, a 2,5-dihydrofuran ring, and a 1,3-dioxole ring; and 5-membered heteroaryl rings such as a furan ring, a thiophen ring, an oxazole ring, an isoxazole ring, a thiazole ring, and an isothiazole ring.

Preferable examples of a substituent on the "5-membered hetero ring" include: halogeno groups such as a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a chloromethyl group, a chloroethyl group, a trifluoromethyl group, a 1,2-dichloro-n-propyl group, and a 1-fluoro-n-butyl group; a hydroxy group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a 2-chloro-n-propoxy group, a 2,3-dichlorobutoxy group, and a trifluoromethoxy group; and a cyano group.

The aromacyclic quaternary ammonium compound of the present invention is not particularly limited by the preparation method thereof. For example, the aromacyclic quaternary ammonium compound of the present invention (hereinafter, may be abbreviated as "the compound of the present invention") may be obtained by the method mentioned in examples using conventionally-known reactions.

The compound of the present invention may also be prepared by the following methods, for example.

Preparation of N-aminoonium Salt

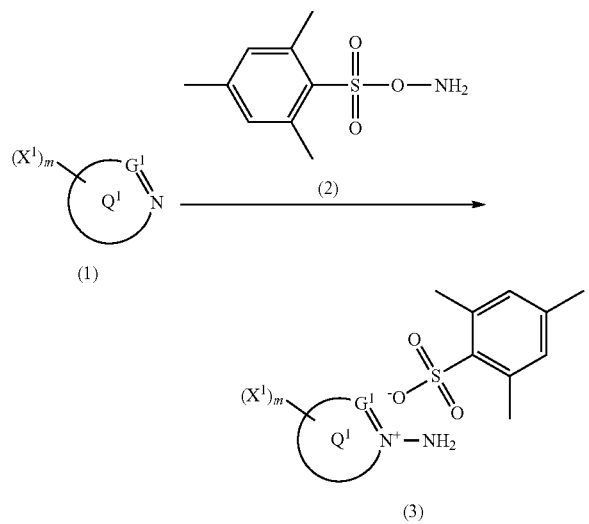

A heteroaryl compound (1) and an O-(mesitylsulfonyl) hydroxylamine (2) are reacted to prepare a N-aminoonium salt (3).

A hydroxylamine O-sulfonate, or an O-(diphenylphosphinyl) hydroxylamine may also be used instead of the O-(mesitylsulfonyl) hydroxylamine.

In the reaction formulae, $G^1$, $Q^1$, $X^1$, and m are the same groups as those in the above-mentioned formulae (I) and (II), respectively.

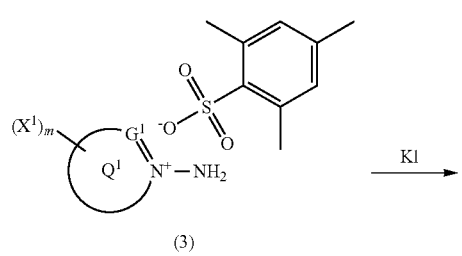

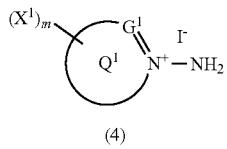

Although the N-aminoonium salt (3) may be directly subjected to the succeeding condensation reaction with a carboxylic acid compound (5), the N-aminoonium salt (3) may be subjected to salt exchange to obtain an N-aminoonium salt (4), which is an iodide salt, in the case where the safety of a substrate is required to be considered.

In the reaction formulae, $G^1$, $Q^1$, $X^1$, and m are the same groups as those in the formulae (I) and (II), respectively.

(Condensation Reaction)

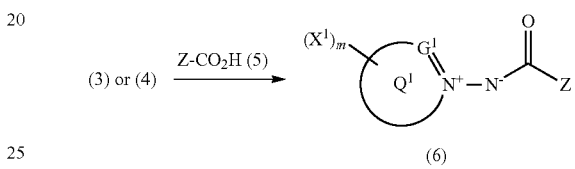

The N-aminoonium salt (3) or (4) and the carboxylic acid compound (5) are condensed in the presence of a condensation agent available in amide synthesis to prepare the compound of the present invention (6).

Examples of the condensation agent include DCC (dicyclohexylcarbodiimide), DIC (diisopropylcarbodiimide), and EDI (1-ethyl-3-(3-dimethylaminopropyl)-carbodiimide).

In the reaction formulae, G, $Q^1$, $X^1$, and m are the same groups as those in the formula (I) and formula (II), respectively, and Z indicates the moiety in which $Q^2$ having $X^2$ and $(X^3)n$ is bound to Y in the formulae (I) and (II). A substituent on $Q^2$ may be changed appropriately after the condensation reaction.

In the case where a compound of formula (I) or (II) in which A is a sulfur atom is prepared, the compound may be prepared by using a dithiocarboxylic acid ester (7) instead of the carboxylic acid compound (5).

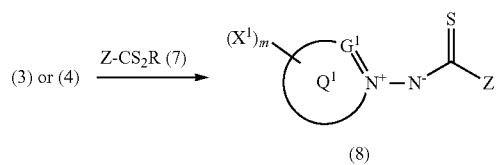

In the condensation reaction with the dithiocarboxylic acid ester (7), a base such as calcium carbonate or sodium ethoxide is preferably used.

In the reaction formulae, $G^1$, $Q^1$, $X^1$, and m are the same groups as those in the formulae (I) and (II), respectively, Z indicates the moiety in which $Q^2$ having $X^2$ and $(X^3)n$ is bound to Y in the formulae (I) and (II), and R is a C1-6 alkyl group such as a methyl group or an ethyl group. A substituent on $Q^2$ may be changed appropriately after the condensation reaction.

The compound of the present invention exhibits excellent control effects against pests, such as various agricultural insect pests or acarians which affect plant growth.

In addition, the compound of the present invention is a highly safe substance as it exhibits low phytotoxicity against crop plants and low toxicity to fish and warm-blooded animals. Thus, the compound of the present invention is useful as an active ingredient of an insecticide or acaricide.

In addition, in recent years, as a result of increased resistance to various existing drugs in many insect pests such as plutellidae, delphacidae, cicadellidae, and aphids, the problem of a lack of efficacy of these drugs has arisen, and thus drugs effective against insect pests in resistant strains are also desired. The compound of the present invention has excellent control effects not only on susceptible strains but also on insect pests of various resistant strains and even acarians of acaricide-resistant strains.

The compound of the present invention has excellent control effects against ectoparasites and endoparasites that cause harm to humans or livestock. In addition, the compound according to the present invention is a highly safe substance as it has low toxicity to fish and warm-blooded animals. Thus, the compound of the present invention is useful as an active ingredient of an ectoparasite-control agent or an endoparasite-control agent.

The compound of the present invention exhibits efficacy in all developmental stages of organisms to be controlled, and exhibits excellent control effects against eggs, nymphs, larvae, pupae, and adults of acarians or insects, for example.

(Pest Control Agent, Insecticide or Acaricide)

A pest control agent, insecticide or acaricide of the present invention contains at least one selected from the compounds of the present invention, as an active ingredient thereof. The amount of the compound of the present invention contained in the pest control agent, insecticide or acaricide of the present invention is not particularly limited, provided that control effects are exhibited against pests, agricultural insect pests or acarians.

It is preferable that the pest control agent, insecticide or acaricide of the present invention be applied to cereals; vegetables; root vegetables; potatoes; flowers and ornamental plants; fruit-bearing trees; foliage plants; trees, such as tea, coffee, or cacao; feed crops; lawn grasses; or plants such as cotton.

In the application to plants, the pest control agent, insecticide or acaricide of the present invention may be applied to any portions, such as leaves, stems, stalks, flowers, buds, fruits, seeds, sprouts, roots, tubers, tuberous roots, shoots, or slips.

The pest control agent, insecticide or acaricide of the present invention is not particularly limited by the species of plant to which it is applied. Examples of the plant species include original species, varieties, improved varieties, cultivars, mutants, hybrid bodies, and gene recombinants (GMO).

The pest control agent according to the present invention may be used to control various agricultural insect pests and acarians by conducting seed treatment, foliage application, soil application, or submerged application.

Specific examples of agricultural insect pests and acarians to be controlled with the pest control agent of the present invention are shown below.

(1) Butterflies and Moths of the Order Lepidoptera
  (a) Moths belonging to the family Arctiidae, such as *Hyphantria cunea*, and *Lemyra imparilis*;
  (b) Moths belonging to the family Bucculatricidae, such as *Bucculatrix pyrivorella*;
  (c) Moths belonging to the family Carposinidae, such as *Carposina sasakii*;
  (d) Moths belonging to the family Crambidae, such as *Diaphania indica*, and *Diaphania nitidalis*, of *Diaphania* spp.; *Ostrinia furnacalis*, *Ostrinia nubilalis*, and *Ostrinia scapulalis*, of *Ostrinia* spp.; and others such as *Chilo suppressalis*, *Cnaphalocrocis medinalis*, *Conogethes punctiferalis*, *Diatraea grandiosella*, *Glyphodes pyloalis*, *Hellula undalis*, and *Parapediasia teterrella*;
  (e) Moths belonging to the family Gelechiidae, such as *Helcystogramma triannulella*, *Pectinophora gossypiella*, *Phthorimaea operculella*, and *Sitotroga cerealella*;
  (f) Moths belonging to the family Geometridae, such as *Ascotis selenaria*;
  (g) Moths belonging to the family Gracillariidae, such as *Caloptilia theivora*, *Phyllocnistis citrella*, and *Phyllonorycter ringoniella*;
  (h) Butterflies belonging to the family Hesperiidae, such as *Parnara guttata*;
  (i) Moths belonging to the family Lasiocampidae, such as *Malacosoma neustria*;
  (j) Moths belonging to the family Lymantriidae, such as *Lymantria dispar*, and *Lymantria monacha*, of *Lymantria* spp.; and others such as *Euproctis pseudoconspersa*, and *Orgyia thyellina*;
  (k) Moths belonging to the family Lyonetiidae, such as *Lyonetia clerkella*, and *Lyonetia prunifoliella malinella*, of *Lyonetia* spp.;
  (l) Moths belonging to the family Noctuidae, such as *Spodoptera depravata*, *Spodoptera eridania*, *Spodoptera exigua*, *Spodoptera frugiperda*, *Spodoptera littoralis*, and *Spodoptera litura*, of *Spodoptera* spp.; *Autographa gamma*, and *Autographa nigrisigna*, of *Autographa* spp.; *Agrotis ipsilon*, and *Agrotis segetum*, of *Agrotis* spp.; *Helicoverpa armigera*, *Helicoverpa assulta*, and *Helicoverpa zea*, of *Helicoverpa* spp.; *Heliothis armigera*, and *Heliothis virescens*, of *Heliothis* spp.; and others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens*, and *Trichoplusia ni*;
  (m) Moths belonging to the family Nolidae, such as *Earias insulana*;
  (n) Butterflies belonging to the family Pieridae, such as *Pieris brassicae*, and *Pieris rapae crucivora*, of *Pieris* spp.;
  (o) Moths belonging to the family Plutellidae, such as *Acrolepiopsis sapporensis*, and *Acrolepiopsis suzukiella*, of *Acrolepiopsis* spp.; and others such as *Plutella xylostella*;
  (p) Moths belonging to the family Pyralidae, such as *Cadra cautella*, *Elasmopalpus lignosellus*, *Etiella zinckenella*, and *Galleria mellonella*;
  (q) Moths belonging to the family Sphingidae, such as *Manduca quinquemaculata*, and *Manduca sexta*, of *Manduca* spp.;
  (r) Moths belonging to the family Stathmopodidae, such as *Stathmopoda masinissa*;
  (s) Moths belonging to the family Tineidae, such as *Tinea translucens*;
  (t) Moths belonging to the family Tortricidae, such as *Adoxophyes honmai*, and *Adoxophyes orana*, of *Adoxophyes* spp.; *Archips breviplicanus*, and *Archips fuscocupreanus* of *Archips* spp.; and others such as *Choristoneura fumiferana*, *Cydia pomonella*, *Eupoecilia ambiguella*, *Grapholitha molesta*, *Homona magn-*

*anima, Leguminivora glycinivorella, Lobesia botrana, Matsumuraeses phaseoli, Pandemis heparana,* and *Sparganothis pilleriana;*
  (u) Moths belonging to the family Yponomeutidae, such as *Argyresthia conjugella.*
(2) Insect Pests of the Order Thysanoptera
  (a) Insect pests belonging to the family Phlaeothripidae, such as *Ponticulothrips diospyrosi;*
  (b) Insect pests belonging to the family Thripidae, such as *Frankliniella intonsa,* and *Frankliniella occidentalis,* of *Frankliniella* spp.; *Thrips palmi,* and *Thrips tabaci,* of *Thrips* spp.; and others such as *Heliothrips haemorrhoidalis,* and *Scirtothrips dorsalis.*
(3) Insect Pests of the Order Hemiptera
(A) the Infraorder Archaeorrhyncha
  (a) Insect pests belonging to the family Delphacidae, such as *Laodelphax striatella, Nilaparvata lugens, Perkinsiella saccharicida,* and *Sogatella furcifera.*
(B) The Infraorder Clypeorrhyncha
  (a) Insect pests belonging to the family Cicadellidae, such as *Empoasca fabae, Empoasca nipponica, Empoasca onukii,* and *Empoasca sakaii,* of *Empoasca* spp.; and others such as *Arboridia apicalis, Balclutha saltuella, Epiacanthus stramineus, Macrosteles striifrons,* and *Nephotettix cinctinceps.*
(C) The Infraorder *Heteroptera*
  (a) Insect pests belonging to the family Alydidae, such as *Riptortus clavatus;*
  (b) Insect pests belonging to the family Coreidae, such as *Cletus punctiger,* and *Leptocorisa chinensis;*
  (c) Insect pests belonging to the family Lygaeidae, such as *Blissus leucopterus, Cavelerius saccharivorus,* and *Togo hemipterus;*
  (d) Insect pests belonging to the family Miridae, such as *Halticus insularis, Lygus lineolaris, Psuedatomoscelis seriatus, Stenodema sibiricum, Stenotus rubrovittatus,* and *Trigonotylus caelestialium;*
  (e) Insect pests belonging to the family Pentatomidae, such as *Nezara antennata,* and *Nezara viridula,* of *Nezara* spp.; *Eysarcoris aeneus, Eysarcoris lewisi,* and *Eysarcoris ventralis,* of *Eysarcoris* spp.; and others such as *Dolycoris baccarum, Eurydema rugosum, Glaucias subpunctatus, Halyomorpha halys, Piezodorus hybneri, Plautia crossota,* and *Scotinophora lurida;*
  (f) Insect pests belonging to the family Pyrrhocoridae, such as *Dysdercus cingulatus;*
  (g) Insect pests belonging to the family Rhopalidae, such as *Rhopalus msculatus;*
  (h) Insect pests belonging to the family Scutelleridae, such as *Eurygaster integriceps*);
  (i) Insect pests belonging to the family Tingidae, such as *Stephanitis nashi.*
(D) The Infraorder Sternorrhyncha
  (a) Insect pests belonging to the family Adelgidae, such as *Adelges laricis;*
  (b) Insect pests belonging to the family Aleyrodidae, such as *Bemisia argentifolii,* and *Bemisia tabaci,* of *Bemisia* spp.; and others such as *Aleurocanthus spiniferus, Dialeurodes citri,* and *Trialeurodes vaporariorum;*
  (c) Insect pests belonging to the family Aphididae, such as *Aphis craccivora, Aphis fabae, Aphis forbesi, Aphis gossypii, Aphis pomi, Aphis sambuci,* and *Aphis spiraecola,* of *Aphis* spp.; *Rhopalosiphum maidis,* and *Rhopalosiphum padi,* of *Rhopalosiphum* spp.; *Dysaphis plantaginea,* and *Dysaphis radicola,* of *Dysaphis* spp.; *Macrosiphum avenae,* and *Macrosiphum euphorbiae,* of *Macrosiphum* spp.; *Myzus cerasi, Myzus persicae,* and *Myzus varians,* of *Myzus* spp.; and others such as *Acyrthosiphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodon humuli, Schizaphis graminum, Sitobion avenae,* and *Toxoptera aurantii;*
  (d) Insect pests belonging to the family Coccidae, such as *Ceroplastes ceriferus,* and *Ceroplastes rubens,* of *Ceroplastes* spp.;
  (e) Insect pests belonging to the family Diaspididae, such as *Pseudaulacaspis pentagona,* and *Pseudaulacaspis prunicola,* of *Pseudaulacaspis* spp.; *Unaspis euonymi,* and *Unaspis yanonensis,* of *Unaspis* spp.; and others such as *Aonidiella aurantii, Comstockaspis perniciosa, Fiorinia theae,* and *Pseudaonidia paeoniae;*
  (f) Insect pests belonging to the family Margarodidae, such as *Drosicha corpulenta,* and *Teerya purchasi;*
  (g) Insect pests belonging to the family Phylloxeridae, such as *Viteus vitifolii;*
  (h) Insect pests belonging to the family Pseudococcidae, such as *Planococcus citri,* and *Planococcus kuraunhiae,* of *Planococcus* spp.; and others such as *Phenacoccus solani,* and *Pseudococcus comstocki;*
  (i) Insect pests belonging to the family Psyllidae, such as *Psylla mali,* and *Psylla pyrisuga,* of *Psylla* spp.; and others such as *Diaphorina citri.*
(4) Insect Pests of the Infraorder *Polyphaga*
  (a) Insect pests belonging to the family Anobiidae, such as *Lasioderma serricorne;*
  (b) Insect pests belonging to the family Attelabidae, such as *Byctiscus betulae,* and *Rhynchites heros;*
  (c) Insect pests belonging to the family Bostrichidae, such as *Lyctus brunneus;*
  (d) Insect pests belonging to the family Brentidae, such as *Cylas formicarius;*
  (e) Insect pests belonging to the family Buprestidae, such as *Agrilus sinuatus;*
  (f) Insect pests belonging to the family Cerambycidae, such as *Anoplophora malasiaca, Monochamus alternatus, Psacothea hilaris,* and *Xylotrechus pyrrhoderus;*
  (g) Insect pests belonging to the family Chrysomelidae, such as *Bruchus pisorum,* and *Bruchus rufimanus,* of *Bruchus* spp.; *Diabrotica barberi, Diabrotica undecimpunctata,* and *Diabrotica virgifera,* of *Diabrotica* spp.; *Phyllotreta nemorum,* and *Phyllotreta striolata,* of *Phyllotreta* spp.; and others such as *Aulacophora femoralis, Callosobruchus chinensis, Cassida nebulosa, Chaetocnema concinna, Leptinotarsa decemlineata, Oulema oryzae,* and *Psylliodes angusticollis;*
  (h) Insect pests belonging to the family Coccinellidae, such as *Epilachna varivestis,* and *Epilachna vigintioctopunctata,* of *Epilachna* spp.;
  (i) Insect pests belonging to the family Curculionidae, such as *Anthonomus grandis,* and *Anthonomus pomorum,* of *Anthonomus* spp.; *Sitophilus granarius,* and *Sitophilus zeamais,* of *Sitophilus* spp.; and others such as *Echinoenemus squameus, Euscepes postfasciatus, Hylobius abietis, Hypera postica, Lissohoptrus oryzophilus, Otiorhynchus sulcatus, Sitona lineatus,* and *Sphenophorus venatus;*
  (j) Insect pests belonging to the family Elateridae, such as *Melanotus fortnumi,* and *Melanotus tamsuyensis,* of *Melanotus* spp.;
  (k) Insect pests belonging to the family Nitidulidae, such as *Epuraea domina;*

(l) Insect pests belonging to the family Scarabaeidae, such as *Anomala cuprea*, and *Anomala rufocuprea*, of *Anomala* spp.; and others such as *Cetonia aurata, Gametis jucunda, Heptophylla picea, Melolontha melolontha*, and *Popillia japonica*;
(m) Insect pests belonging to the family Scolytidae, such as *Ips typographus*;
(n) Insect pests belonging to the family Staphylinidae, such as *Paederus fuscipes*;
(o) Insect pests belonging to the family Tenebrionidae, such as *Tenebrio molitor*, and Tribolium castaneum;
(p) Insect pests belonging to the family Trogossitidae, such as *Tenebroides mauritanicus*.

(5) Insect Pests of the Order Diptera (A) the Infraorder Brachycera
  (a) Insect pests belonging to the family Agromyzidae, such as *Liriomyza bryoniae, Liriomyza chinensis, Liriomyza sativae*, and *Liriomyza trifolii*, of *Liriomyza* spp.; and others such as *Chromatomyia horticola*, and *Agromyza oryzae*;
  (b) Insect pests belonging to the family Anthomyiidae, such as *Delia platura*, and *Delia radicum*, of *Delia* spp.; and others such as *Pegomya cunicularia*;
  (c) Insect pests belonging to the family Drosophilidae, such as *Drosophila melanogaster*, and *Drosophila suzukii*, of *Drosophila* spp.;
  (d) Insect pests belonging to the family Ephydridae, such as *Hydrellia griseola*;
  (e) Insect pests belonging to the family Psilidae, such as *Psila rosae*;
  (f) Insect pests belonging to the family Tephritidae, such as *Bactrocera cucurbitae*, and *Bactrocera dorsalis*, of *Bactrocera* spp.; *Rhagoletis cerasi*, and *Rhagoletis pomonella*, of *Rhagoletis* spp.; and others such as *Ceratitis capitata*, and *Dacus oleae*.

(B) The Infraorder Nematocera
  (a) Insect pests belonging to the family Cecidomyiidae, such as *Asphondylia yushimai, Contarinia sorghicola, Mayetiola destructor*, and *Sitodiplosis mosellana*.

(6) Insect Pests of the Order Orthoptera
  (a) Insect pests belonging to the family Acrididae, such as *Schistocerca americana*, and *Schistocerca gregaria*, of *Schistocerca* spp.; and others such as *Chortoicetes terminifera, Dociostaurus maroccanus, Locusta migratoria, Locustana pardalina, Nomadacris septemfasciata*, and *Oxya yezoensis*;
  (b) Insect pests belonging to the family Gryllidae, such as *Acheta domestica*, and *Teleogryllus emma*;
  (c) Insect pests belonging to the family Gryllotalpidae, such as *Gryllotalpa orientalis*;
  (d) Insect pests belonging to the family Tettigoniidae, such as *Tachycines asynamorus*.

(7) Acarians (Acari)

(A) Acaridida of the Order *Astigmata*
  (a) Acarians belonging to the family Acaridae, such as *Rhizoglyphus echinopus*, and *Rhizoglyphus robini*, of *Rhizoglyphus* spp.; *Tyrophagus neiswanderi, Tyrophagus perniciosus, Tyrophagus putrescentiae*, and *Tyrophagus similis*, of *Tyrophagus* spp.; and others such as *Acarus siro, Aleuroglyphus ovatus*, and *Mycetoglyphus fungivorus*;

(B) Actinedida of the Order Prostigmata
  (a) Acarians belonging to the family Tetranychidae, such as *Bryobia praetiosa*, and *Bryobia rubrioculus*, of *Bryobia* spp.; *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis*, and *Eotetranychus uncatus*, of *Eotetranychus* spp.; *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii*, and *Oligonychus ununguis*, of *Oligonychus* spp.; *Panonychus citri, Panonychus mori*, and *Panonychus ulmi*, of *Panonychus* spp.; *Tetranychus cinnabarinus, Tetranychus evansi, Tetranychus kanzawai, Tetranychus ludeni, Tetranychus quercivorus, Tetranychus phaselus, Tetranychus urticae*, and *Tetranychus viennensis*, of *Tetranychus* spp.; *Aponychus corpuzae*, and *Aponychus firmianae*, of *Aponychus* spp.; *Sasanychus akitanus*, and *Sasanychus pusillus*, of *Sasanychus* spp.; *Shizotetranychus celarius, Shizotetranychus longus, Shizotetranychus miscanthi, Shizotetranychus recki*, and *Shizotetranychus schizopus*, of *Shizotetranychus* spp.; and others such as *Tetranychina harti, Tuckerella pavoniformis*, and *Yezonychus sapporensis*;
  (b) Acarians belonging to the family Tenuipalpidae, such as *Brevipalpus lewisi, Brevipalpus obovatus, Brevipalpus phoenicis, Brevipalpus russulus*, and *Brevipalpus californicus*, of *Brevipalpus* spp.; *Tenuipalpus pacificus*, and *Tenuipalpus zhizhilashviliae*, of *Tenuipalpus* spp.; and others such as *Dolichotetranychus floridanus*;
  (c) Acarians belonging to the family Eriophyidae, such as *Aceria diospyri, Aceria ficus, Aceria japonica, Aceria kuko, Aceria paradianthi, Aceria tiyingi, Aceria tulipae*, and *Aceria zoysiea*, of *Aceria* spp.; *Eriophyes chibaensis*, and *Eriophyes emarginatae*, of *Eriophyes* spp.; *Aculops lycopersici*, and *Aculops pelekassi*, of *Aculops* spp.; *Aculus fockeui*, and *Aculus schlechtendali*, of *Aculus* spp.; and others such as *Acaphylla theavagrans, Calacarus carinatus, Colomerus vitis, Calepitrimerus vitis, Epitrimerus pyri, Paraphytoptus kikus, Paracalacarus podocarpi*, and *Phyllocotruta citri*;
  (d) Acarians belonging to the family Transonemidae, such as *Tarsonemus bilobatus*, and *Tarsonemus waitei*, of *Tarsonemus* spp.; and others such as *Phytonemus pallidus*, and *Polyphagotarsonemus latus*;
  (e) Acarians belonging to the family Penthaleidae, such as *Penthaleus erythrocephalus*, and *Penthaleus major*, of *Penthaleus* spp.

The pest control agent of the present invention may be mixed or used with other active ingredients of fungicides, insecticides, acaricides, nematicides, or soil insect pest control agents, or plant regulatory agents, synergists, fertilizers, soil improvement agents, or animal feeds.

The combination of the compound of the present invention with other active ingredients may exhibit synergistic effects on insecticidal, acaricidal, or nematicidal activity. The synergistic effects can be confirmed by a commonly used method using the Colby formula (Colby. S. R., Calculating Synergistic and Antagonistic Responses of Herbicide Combinations; Weeds 15, pages 20 to 22, 1967).

Specific examples of the insecticides, acaricides, nematicides, soil insect pest control agents, and anthelmintic agents which can be mixed or used with the pest control agent of the present invention are shown below.

(1) Acetylcholinesterase inhibitors:
  (a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb, fenothiocarb, aldoxycarb, allyxycarb, aminocarb, bufencarb, chloethocarb, fentiocarb, promecarb;
(b) Organophosphate-based: acephate, azamethiphos, azinphos-ethyl, azinphos-methyl, cadusafos, chloroethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl=O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion, bromophos-ethyl, cyanofenphos, demeton-S methyl sulfone, dialifos, dichlofenthion, dioxabenzofos, etrimfos, fensulfothion, fonofos, formothion, isazophos, iodofenphos, isocarbophos, methacrifos, pirimiphos-ethyl, phosphocarb, propaphos, prothoate, sulprophos.
(2) GABAergic chloride ion channel antagonists: acetoprole, chlordene, endosulfan, ethiprole, fipronil, pyrafluprole, pyriprole, camphlechlor, heptachlor, dienochlor, flufiprole.
(3) Sodium channel modulators: acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrin, resmethrin, silafluofen, tetramethrin, tetramethrin [(1R)-isomer], tralomethrin, transfluthrin, profluthrin, dimefluthrin, bioethanomethrin, biopermethrin, transpermethrin, fenfluthrin, fenpirithrin, flufenprox, metofluthrin, protrifenbute, terallethrin.
(4) Nicotinic acetylcholine receptor agonist: acetamiprid, clothianidin, dinotefuran, imidacloprid, nitenpyram, nithiazine, thiacloprid, thiamethoxam, sulfoxaflor, nicotine, flupyradifurone, flupyrimin, triflumezopyrim, dicloromezotiaz.
(5) Nicotinic acetylcholine receptor allosteric modulators: spinetoram, spinosad.
(6) Chloride channel activators: abamectin, emamectin, emamectin benzoate, lepimectin, milbemectin, ivermectin, selamectin, doramectin, eprinomectin, moxidectin.
(7) Juvenile hormone-like substances: hydroprene, kinoprene, methoprene, fenoxycarb, pyriproxyfen, diofenolan, epofenonane, triprene.
(8) Other non-specific inhibitors: methyl bromide, halogenated alkyls, chloropicrin, sodium aluminum fluoride, sulfuryl fluoride, borax, boracic acid, disodium octaborate, sodium borate, sodium metaborate, tartar emetic, dazomet, metam, metam-potassium, metam-sodium.
(9) Homoptera selective feeding inhibitors: flonicamid, pymetrozine, pyrifluquinazon, afidopyropen.
(10) Acarian growth inhibitors: clofentezine, diflovidazin, hexythiazox, etoxazole.
(11) Insectan midgut inner membrane disrupting agent derived from microorganisms: *Bacillus thuringiensis* subspecies Isuraerenshi, *Bacillus sphaericus*, *Bacillus thuringiensis* subsp. Aizawai, *Bacillus thuringiensis* subspecies Kurstaki, *Bacillus thuringiensis* subspecies Tenebrionis, Bt crop protein, Cry1Ab, Cry1Ac, Cry1Fa, Cry1A.105, Cry2Ab, Vip3A, mCry3A, Cry3Ab, Cry3Bb, Cry34Ab1/Cry35Ab1.
(12) Mitochondrial ATP biosynthetic enzyme inhibitors: diafenthiuron, azocyclotin, cyhexatin, fenbutatin oxide, propargite, tetradifon.
(13) Oxidative phosphorylation uncouplers: chlorfenapyr, sulfluramid, DNOC, binapacryl, dinobuton, dinocap.
(14) Nicotinic acetylcholine receptor channel blockers: bensultap, cartap hydrochloride, thiosultap-sodium, thiocyclam.
(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron.
(16) Diptera molting disrupting agents: cyromazine.
(17) Molting hormone receptor agonists: chromafenozide, halofenozide, methoxyfenozide, tebufenozide.
(18) Octopamine receptor agonists: amitraz, chlordimeform.
(19) Mitochondrial electron transport system complex III inhibitors: acequinocyl, fluacrypyrim, hydramethylnon, bifenazate.
(20) Mitochondrial electron transport system complex 1 inhibitors: fenazaquin, fenpyroximate, pyrimidifen, pyridaben, tebufenpyrad, tolfenpyrad, rotenone.
(21) Voltage-dependent sodium channel blockers: indoxacarb, metaflumizone.
(22) Acetyl CoA carboxylase inhibitors: spirodiclofen, spiromesifen, spirotetramat, spiropidion.
(23) Mitochondrial electron transport system complex IV inhibitors: aluminum phosphide, calcium phosphide, phosphine, zinc phosphide, cyanide.
(24) Mitochondrial electron transport system complex II inhibitors: cyenopyrafen, cyflumetofen, pyflubumide.
(25) Ryanodine receptor modulators: chlorantraniliprole, cyantraniliprole, flubendiamide, cyclaniliprole, tetraniliprole, cyhalodiamide, tetrachlorantraniliprole.
(26) GABAergic chloride ion channel allosteric modulator: broflanilide, fluxametamide, isocycloseram, afoxolaner, fluralaner, lotilaner, sarolanar.
(27) Other agents (mechanisms of which are unknown): acynonapyr, azadirachtin, benzoximate, bromopropylate, chinomethionat, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimin, fluphenazine, gossyplure, japonilure, metoxadiazone, petroleum, sodium oleate, tetrasul, triarathene, afidopyropen, flometoquin, fluensulfone, meperfluthrin, tetramethylfluthrin, tralopyril, methylneodecanamide, triflumezopyrim, dicloromezotiaz, oxazosulfyl, tyclopyrazoflor.

(28) Anthelmintic agents:
(a) Benzimidazole-based: fenbendazole, albendazole, triclabendazole, oxibendazole, mebendazole, oxfendazole, parbendazole, flubendazole, febantel, netobimin, thiophanate, thiabendazole, cambendazole;
(b) Salicylanilide-based: closantel, oxyclozanide, rafoxanide, niclosamide;
(c) Substituted phenol-based: nitroxinil, nitroscanate;
(d) Pyrimidine-based: pyrantel, morantel;
(e) Imidazothiazole-based: levamisole, tetramisole;
(f) Tetrahydropyrimidine-based: praziquantel, epsiprantel;
(g) Other anthelmintic agents: cyclodiene, ryania, clorsulon, metronidazole, demiditraz, piperazine, diethylcarbamazine, dichlorophene, monepantel, tribendimidine, amidantel, thiacetarsamide, melarsomine, arsenamide.

Specific examples of fungicides which may be mixed or used with the pest control agent of the present invention are shown below.

(A) Nucleic Acid Biosynthesis Inhibitors
(a) RNA polymerase I inhibitors: benalaxyl, benalaxyl-M, furalaxyl, metalaxyl, metalaxyl-M, oxadixyl, clozylacon, ofurace.
(b) Adenosine deaminase inhibitors: bupirimate, dimethirimol, ethirimol.
(c) DNA/RNA synthesis inhibitors: hymexazol, octhilinone.
(d) DNA topoisomerase II inhibitors: oxolinic acid.
(2) Karyokinesis Inhibitors and Cell Division Inhibitors
(a) β-Tubulin polymerization inhibitors: benomyl, carbendazim, fuberidazole, thiabendazole, thiophanate, thiophanate-methyl, diethofencarb, zoxamide, ethaboxam; chlorfenazole, debacarb, trichlaamide, zarilamide.
(b) Cell division inhibitors: pencycuron.
(c) Delocalization inhibitors of spectrin-like protein: fluopicolide, fluopimomide.
(d) Actin/myosin/fimbrin inhibitors: phenamacril, metrafenone, pyriofenone.
(3) Respiration Inhibitor:
(a) Complex I NADH oxidation-reduction inhibitor: diflumetorim; tolfenpyrad, fenazaquin;
(b) Complex II succinic acid dehydrogenase inhibitor: benodanil, flutolanil, mepronil, isofetamid, fluopyram, fenfuram, carboxin, oxycarboxin, thifluzamide, benzovindiflupyr, bixafen, fluxapyroxad, furametpyr, inpyrfluxam, isopyrazam, penflufen, penthiopyrad, sedaxane, isoflucypram, pydiflumetofen, boscalid, pyraziflumid, furmecyclox;
(c) Complex III ubiquinol oxidase Qo inhibitor: azoxystrobin, coumoxystrobin, coumethoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, pyribencarb, metyltetraprole;
(d) Complex III ubiquinol reductase Qi inhibitor: cyazofamid, amisulbrom;
(e) Oxidative phosphorylation uncoupling agent: binapacryl, meptyldinocap, dinocap, fluazinam, ferimzone;
(f) Oxidative phosphorylation inhibitor (ATP synthase inhibitor): fenthin acetate, fentin chloride, fentin hydroxide;
(g) ATP production inhibitor: silthiofam;
(h) Complex III cytochrome bc1 (ubiquinone reductase) Qx (unknown) inhibitor: ametoctradin.

(4) Amino Acid and Protein Synthesis Inhibitor
(a) Methionine biosynthesis inhibitor: cyprodinil, mepanipyrim, pyrimethanil;
(b) Protein synthesis inhibitor: blasticidin-S, kasugamycin, kasugamycin hydrochloride, streptomycin, oxytetracycline.
(5) Signal Transfer Inhibitor:
(a) Signal transfer inhibitor: quinoxyfen, proquinazid;
(b) MAP/histidine kinase inhibitor in osmotic pressure signal transfer: fenpiconil, fludioxonil, chlozolinate, dimethachlon, iprodione, procymidone, vinclozolin.
(6) Lipid and Cell Membrane Synthesis Inhibitor:
(a) Phospholipid biosynthesis and methyltransferase inhibitor: edifenphos, iprobenfos, pyrazophos, isoprothiolane;
(b) Lipid peroxide agent: biphenyl, chloroneb, dichloran, quintozene, tecnazene, tolclofos methyl, etridiazole;
(c) Agents affecting cell membrane: iodocarb, propamocarb, propamocarb hydrochloride, propamocarb-fosetylate, prothiocarb;
(d) Microorganisms disturbing cell membrane of pathogenic bacteria: *Bacillus subtilis*, *Bacillus subtilis* strain QST713, *Bacillus subtilis* strain FZB24, *Bacillus subtilis* strain MBI600, *Bacillus subtilis* strain D747;
(e) Agents disturbing cell membrane: *melaleuca* alternifolia (tea tree) extract; (f) Agents affecting ergosterol: natamycin;
(g) Agents affecting lipid homeostasis and transport/storage: oxathiapiprolin, fluoxapiprolin.
(7) Cell Membrane Sterol Biosynthesis Inhibitor:
(a) C14 position demethylation inhibitor in sterol biosynthesis: triforine; pyrifenox, pyrisoxazole, fenarimol, nuarimol, imazalil, imazalil-sulphate, oxpoconazole, pefurazoate, prochloraz, triflumizole, azaconazole, bitertanol, bromconazole, cyproconazole, difenoconazole, diniconazole, diniconazole-M, epoxyconazole, etaconazole, fenbuconazole, fluquinconazole, flusilazole, flutriafol, hexaconazole, imibenconazole, ipuconazole, metconazole, myclobutanil, penconazole, propiconazole, simeconazole, tebuconazole, tetraconazole, triadimefon, triadimenol, triticonazole, prothioconazole, furconazole, furconazole-cis, diniconazole-M;
(b) Δ14 reductase and Δ8→Δ7-isomerase inhibitor in sterol biosynthesis: aldimorph, dodemorph, dodemorph-acetate, fenpropimorph, tridemorph, fenpropidine, piperalin, spiroxamine, buthiobate;
(c) 3-Keto reductase inhibitor in C4 position demethylation in sterol biosynthesis system: fenhexamid, fenpyrazamine;
(d) Squalene epoxidase inhibitor in sterol biosynthesis system: pyributicarb, naftifen, terbinafine.
(8) Cell Wall Synthesis Inhibitor
(a) Chitin synthetase inhibitor: polyoxin, polyoxorim;
(b) Cellulose synthetase inhibitor: dimethomorph, flumorph, pyrimorph, benthiavalicarb, iprovalicarb, valifenalate, mandipropamide.
(9) Melanin Biosynthesis Inhibitor
(a) Reductase inhibitor in melanin biosynthesis: fthalide, pyroquilon, tricyclazole;
(b) Anhydrase inhibitor in melanin biosynthesis: carpropamid, diclocymet, fenoxanil.
(10) Resistance-Inducing Agents of Host Plant:
(a) Agents affecting salicylic acid synthetic pathway: acibenzolar-s-methyl;

(b) Others: probenazole, tiadinil, isotianil, laminarin, extract liquid of *Reynoutria sachalinensis*, fosetyl, phosphorus acid and salt, fosetyl-calcium, fosetyl-sodium.
(11) Agents of which the activity is unknown: cymoxanil, tecloftalam, triazoxide, flusulfamide, diclomezine, methasulfocarb, cyflufenamid, dodine, dodine free base, flutianil, tebufloquin, picarbutrazox, validamycin; bethoxazin, cyprofuram, flumetover, nitrothal isopropyl, propamidine; florylpicoxamid, ipflufenoquin, pyridachlometyl, pyrapropoyne, aminopyrifen, dichlobentiazox, ipfentrifluconazole, mefentrifluconazole, quinofumelin, dipymetitrone.
(12) Agent having multiple activities: copper (copper salt), bordeaux mixture, copper hydroxide, copper naphthalate, copper oxide, oxychloride copper, copper sulfate, sulfur, sulfur product, calcium polysulfide, ferbam, manzeb, maneb, metiram, propineb, thiuram, zinc thiazole, zineb, ziram, captan, captafol, folpet, chlorothalonil, dichlofluanid, tolylfluanid, guazatine, iminoctadine triacetate, iminoctadine trialbesilate, anilazine, dithianon, chinomethionat, fluoroimide, metasulfotap, dazomet, curfraneb, mancopper, polycarbamate.
(13) Other agents: DBEDC, fluor folpet, chloropicrin, agrobacterium, diphenylamine, methyl isothiocyanate (MITC), mildew-mycin, capsaicin, cyprosulfamide, difenzoquat, difenzoquat-methyl sulfonate, irmamycin, oxamocarb, puropamocin sodium, pyrrolnitrin, tolnifanide, algophase, amicarthiazol, benthiazole.

Specific examples of plant regulatory agents which can be mixed or used with the pest control agent of the present invention are shown below.

1-Methylcyclopropene, 2,3,5-triiodobenzoic acid, IAA, IBA, MCPA, MCPB, 4-CPA, 5-aminolevulinic acid hydrochloride, 6-benzylaminopurine, abscisic acid, aviglycine hydrochloride, ancymidol, butralin, calcium carbonate, calcium chloride, calcium formate, calcium peroxide, lime sulfur, calcium sulfate, chlormequat chloride, chlorpropham, choline chloride, cloprop, cyanamide, cyclanilide, daminozide, decyl alcohol, dichlorprop, dikegulac, dimethipin, diquat, ethephon, ethychlozate, flumetralin, flurprimidol, forchlorfenuron, gibberellin A, gibberellin A3, hymexazol, inabenfide, isoprothiolane, kinetin, maleic acid hydrazide, mefluidide, mepiquat chloride, oxidation type glutathione, paclobutrazol, pendimethalin, prohexadione calcium, prohydrojasmon, pyraflufen-ethyl, sintofen, sodium 1-naphthalene acetate, sodium cyanate, streptomycin, thidiazuron, triapenthenol, tribufos, trinexapac-ethyl, uniconazole P, and 1-nathtylacetamide.

(Ectoparasite Control Agent)

An ectoparasite control agent of the present invention contains at least one selected from the aromacyclic quaternary ammonium compounds of the present invention as an active ingredient thereof. The amount of the compound of the present invention contained in the ectoparasite control agent of the present invention is not particularly limited within the range in which ectoparasite control effects are exhibited.

Examples of host animals to be treated with the ectoparasite control agent of the present invention include warm-blooded animals such as: pet animals such as dogs or cats; pet birds; farm animals such as cattle, horses, pigs, and sheep; and poultry. Additional examples thereof include honey-bees, stag beetles, and unicorn beetles.

The ectoparasite control agent of the present invention may be applied by a known veterinary method (topical, oral, parenteral or subcutaneous administration). Examples of the method include: a method in which a tablet, capsule or feed mixed with the ectoparasite control agent is orally administered to the animals; a method in which an immersion liquid, suppository or injection (intramuscular, subcutaneous, intravenous, intraabdominal or the like) is administered to the animals; a method in which an oil-based or aqueous liquid preparation is topically administered by conducting spraying, pouring on, spotting on or the like; and a method in which the ectoparasite control agent is kneaded into a resin, and the resultant kneaded product is molded in an appropriate form such as a collar or an ear tag, and then topically administered to animals.

Ectoparasites parasitize host animals, especially parasitize in or on the body of warm-blooded animals. More specifically, ectoparasites parasitize the back, armpit, underbelly, inner thigh or the like of host animals and obtain nutritional sources such as blood or dandruff from animals to live. Examples of ectoparasites include acarians, lice, fleas, mosquitoes, stable flies, and flesh flies. Specific examples of ectoparasites which can be controlled by the ectoparasite control agent of the present invention are shown below.

(1) Acarians (Acari)

Acarians belonging to the family Dermanyssidae, acarians belonging to the family Macronyssidae, acarians belonging to the family Laelapidae, acarians belonging to the family Varroidae, acarians belonging to the family Argasidae, acarians belonging to the family Ixodidae, acarians belonging to the family Psoroptidae, acarians belonging to the family Sarcoptidae, acarians belonging to the family Knemidokoptidae, acarians belonging to the family Demodixidae, acarians belonging to the family Trombiculidae, and insect-parasitic acari such as Coleopterophagus berlesei.

(2) Order Phthiraptera

Lice belonging to the family Haematopinidae, lice belonging to the family Linognathidae, biting lice belonging to the family Menoponidae, biting lice belonging to the family Philopteridae, and biting lice belonging to the family Trichodectidae.

(3) Order Siphonaptera

Fleas belonging to the family Pulicidae, such as *Ctenocephalides canis* and *Ctenocephalides felis* of *Ctenocephalides* spp.; fleas belonging to the family Tungidae, fleas belonging to the family Ceratophyllidae, and fleas belonging to the family Leptopsyllidae.

(4) Order Hemiptera.

(5) Insect Pests of the Order Diptera

Mosquitoes belonging to the family Culicidae, black flies belonging to the family Simuliidae, punkie belonging to the family Ceratopogonidae, horseflies belonging to the family Tabanidae, flies belonging to the family Muscidae, tsetse flies belonging to the family Glossinidae, flesh flies belonging to the family Sarcophagidae, flies belonging to the family Hippoboscidae, flies belonging to the family Calliphoridae, and flies belonging to the family Oestridae.

(Endoparasite Control Agent or Expellant)

An endoparasite control agent or expellant of the present invention contains at least one selected from the aromacyclic quaternary ammonium compounds of the present invention as an active ingredient thereof. The amount of the compound of the present invention contained in the endoparasite control agent or expellant of the present invention is not particularly limited within the range in which endoparasite control effects are exhibited.

Parasites to be controlled or expelled by the endoparasite control agent or expellant of the present invention parasitize in host animals, particularly in warm-blooded animals or fish (endoparasite). Examples of the host animals on which the endoparasite control agent or expellant of the present invention is effective include: warm-blooded animals such as humans, domestic mammals (such as cows, horses, pigs, sheep, and goats), laboratory animals (such as mice, rats, and jirds), pet animals (such as hamsters, guinea pigs, dogs, cats, horses, squirrels, rabbits, and ferrets), mammals in nature or zoos (such as monkeys, foxes, deer, and buffalos), poultry (such as turkeys, ducks, chickens, quail, and geese), and pet birds (such as pigeons, parrots, magpies, java sparrows, parakeets, finches, and canaries); and fish such as salmon, trout, and koi carp. It is possible to prevent or treat parasitic diseases mediated by parasites by controlling or expelling the parasites.

Examples of the parasites to be controlled or expelled include the following.

(1) Nematodes of the Order Dioctophymatida
  (a) Kidney worms belonging to the family Dioctophymatidae, such as *Dioctophyma renale* of *Dioctophyma* spp.; and
  (b) kidney worms belonging to the family Soboliphymatidae, such as *Soboliphyme abei* and *Soboliphyme baturini* of *Soboliphyme* spp.

(2) Nematodes of the Order Trichocephalida
  (a) Trichinae belonging to the family Trichinellidae, such as *Trichinella spiralis* of *Trichinella* spp.; and
  (b) whipworms belonging to the family Trichuridae, such as *Capillaria annulata, Capillaria contorta, Capillaria hepatica, Capillaria perforans, Capillaria plica,* and *Capillaria suis*, of *Capillaria* spp.; and *Trichuris vulpis, Trichuris discolor, Trichuris ovis, Trichuris skrjabini*, and *Trichuris suis*, of *Trichuris* spp.

(3) Nematodes of the Order Rhabditida
  *Strongyloides stercoralis* belonging to the family Strongyloididae, such as *Strongyloides papillosus, Strongyloides planiceps, Strongyloides ransomi, Strongyloides suis, Strongyloides stercoralis, Strongyloides tumefaciens,* and *Strongyloides ratti*, of *Strongyloides* spp.

(4) Nematodes of the Order Strongylida
  Ancylostomas belonging to the family Ancylostomatidae, such as *Ancylostoma braziliense, Ancylostoma caninum, Ancylostoma duodenale,* and *Ancylostoma tubaeforme,* of *Ancylostoma* spp.; *Uncinaria stenocephala* of *Uncinaria* spp.; and *Bunostomum phlebotomum,* and *Bunostomum trigonocephalum,* of *Bunostomum* spp.

(5) Nematodes of the Order Strongylida
  (a) Nematodes belonging to the family Angiostrongylidae, such as *Aelurostrongylus abstrusus* of *Aelurostrongylus* spp.; and *Angiostrongylus vasorum,* and *Angiostrongylus cantonesis,* of *Angiostrongylus* spp.;
  (b) nematodes belonging to the family Crenosomatidae, such as *Crenosoma aerophila,* and *Crenosoma vulpis,* of *Crenosoma* spp.;
  (c) nematodes belonging to the family Filaroididae, such as *Filaroides hirthi,* and *Filaroides osleri,* of *Filaroides* spp.;
  (d) metastrongyles belonging to the family Metastrongylidae, such as *Metastrongylus apri, Metastrongylus asymmetricus, Metastrongylus pudendotectus,* and *Metastrongylus salmi,* of *Metastrongylus* spp.; and
  (e) gapeworms belonging to the family Syngamidae, such as *Cyathostoma bronchialis* of *Cyathostoma* spp.; and *Syngamus skrjabinomorpha,* and *Syngamus trachea,* of *Syngamus* spp.

(6) Nematodes of the Order Strongylida
  (a) Nematodes belonging to the family Molineidae, such as *Nematodirus filicollis,* and *Nematodirus spathiger,* of *Nematodirus* spp.;
  (b) nematodes belonging to the family Dictyocaulidae, such as *Dictyocaulus filaria,* and *Dictyocaulus viviparus,* of *Dictyocaulus* spp.;
  (c) nematodes belonging to the family Haemonchidae, such as *Haemonchus contortus* of *Haemonchus* spp.; and *Mecistocirrus digitatus* of *Mecistocirrus* spp.;
  (d) nematodes belonging to the family Haemonchidae, such as *Ostertagia ostertagi* of *Ostertagia* spp.;
  (e) nematodes belonging to the family Heligmonellidae, such as *Nippostrongylus braziliensis* of *Nippostrongylus* spp.; and
  (f) nematodes belonging to the family Trichostrongylidae, such as *Trichostrongylus axei, Trichostrongylus colubriformis,* and *Trichostrongylus tenuis,* of *Trichostrongylus* spp.; *Hyostrongylus rubidus* of *Hyostrongylus* spp.; and *Obeliscoides cuniculi* of *Obeliscoides* spp.

(7) Nematodes of the Order Strongylida
  (a) Nematodes belonging to the family Chabertiidae, such as *Chabertia ovina* of *Chabertia* spp.; and *Oesophagostomum brevicaudatum* (pig), *Oesophagostomum columbianum, Oesophagostomum dentatum, Oesophagostomum georgianum* (pig), *Oesophagostomum maplestonei, Oesophagostomum quadrispinulatum* (pig), *Oesophagostomum radiatum, Oesophagostomum venulosum,* and *Oesophagostomum watanabei* (hog), of *Oesophagostomum* spp.;
  (b) nematodes belonging to the family Stephanuridae, such as *Stephanurus dentatus* of *Stephanurus* spp.; and
  (c) nematodes belonging to the family Strongylidae, such as *Strongylus asini, Strongylus edentatus, Strongylus equinus,* and *Strongylus vulgaris,* of *Strongylus* spp.

(8) Nematodes of the Order Oxyurida
  Nematodes belonging to the family Oxyuridae, such as *Enterobius anthropopitheci,* and *Enterobius vermicularis,* of *Enterobius* spp.; *Oxyuris equi* of *Oxyuris* spp.; and *Passalurus ambiguus* of *Passalurus* spp.

(9) Nematodes of the Order Ascaridida
  (a) Nematodes belonging to the family Ascaridiidae, such as *Ascaridia galli* of *Ascaridia* spp.;
  (b) nematodes belonging to the family Heterakidae, such as *Heterakis beramporia, Heterakis brevispiculum, Heterakis gallinarum, Heterakis pusilla,* and *Heterakis putaustralis,* of *Heterakis* spp.;
  (c) nematodes belonging to the family Anisakidae, such as *Anisakis simplex* of *Anisakis* spp.;
  (d) nematodes belonging to the family Ascarididae, such as *Ascaris lumbricoides,* and *Ascaris suum,* of *Ascaris* spp.; and *Parascaris equorum* of *Parascaris* spp.; and
  (e) nematodes belonging to the family Toxocaridae, such as *Toxocara canis, Toxocara leonina, Toxocara suum, Toxocara vitulorum,* and *Toxocara cati,* of *Toxocara* spp.

(10) Nematodes of the Order Spirurida
  (a) Nematodes belonging to the family Onchocercidae, such as *Brugia malayi, Brugia pahangi,* and *Brugia patei,* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis, Onchocerca gibsoni,* and *Onchocerca gutturosa,* of *Onchocerca* spp.;
  (b) nematodes belonging to the family Setariidae, such as *Setaria digitata, Setaria equina, Setaria labiatopapil-*

*losa*, and *Setaria marshalli*, of *Setaria* spp.; and *Wuchereria bancrofti* of *Wuchereria* spp.; and
(c) nematodes belonging to the family Filariidae, such as *Parafilaria multipapillosa* of *Parafilaria* spp.; and *Stephanofilaria assamensis, Stephanofilaria dedoesi, Stephanofilaria kaeli, Stephanofilaria okinawaensis,* and *Stephanofilaria stilesi* of *Stephanofilaria* spp.

(11) Nematodes of the Order Spirurida
(a) Nematodes belonging to the family Gnathostomatidae, such as *Gnathostoma doloresi*, and *Gnathostoma spinigerum*, of *Gnathostoma* spp.;
(b) nematodes belonging to the family Habronematidae, such as *Habronema majus, Habronema microstoma,* and *Habronema muscae*, of *Habronema* spp.; and *Draschia megastoma* of *Draschia* spp.;
(c) nematodes belonging to the family Physalopteridae, such as *Physaloptera canis, Physaloptera cesticillata, Physaloptera erdocyona, Physaloptera felidis, Physaloptera gemina, Physaloptera papilloradiata, Physaloptera praeputialis, Physaloptera pseudopraerutialis, Physaloptera rara, Physaloptera sibirica,* and *Physaloptera vulpineus*, of *Physaloptera* spp.;
(d) nematodes belonging to the family Gongylonematidae, such as *Gongylonema pulchrum* of *Gongylonema* spp.;
(e) nematodes belonging to the family Spirocercidae, such as *Ascarops strongylina* of *Ascarops* spp.; and
(f) nematodes belonging to the family Thelaziidae, such as *Thelazia callipaeda, Thelazia gulosa, Thelazia lacrymalis, Thelazia rhodesi,* and *Thelazia skrjabini*, of *Thelazia* spp.

(Control Agent Against Other Pests)

In addition, the compound of the present invention exhibits an excellent effect of controlling insect pests that have a sting or venom that can harm humans or livestock, insect pests carrying various pathogens/pathogenic bacteria, or insect pests that impart a discomforting sensation to humans (such as toxic insect pests, sanitary insect pests, or unpleasant insect pests).

Specific examples thereof are shown below.
(1) Insect Pests of the Order Hymenoptera Sawflies belonging to the family Argidae, wasps belonging to the family Cynipidae, sawflies belonging to the family Diprionidae, ants belonging to the family Formicidae, wasps belonging to the family Mutillidae, and wasps belonging to the family Vespidae.
(2) Other Insect Pests Blattodea, termite, araneae, cetipede, millipede, crustacea and *Cimex lectularius*.

(Preparation Formulation)

Although some preparation formulations of the pest control agent, insecticide, acaricide, ectoparasite control agent, endoparasite control agent or expellant of the present invention are shown below, additives and addition amounts thereof are not limited to these examples, and may be varied in a wide range. In the preparation formulation, the term "part" indicates "parts by mass" and the term "%" indicates "% by mass".

The agricultural, horticultural or paddy preparation formulations are shown below.

(Formulation 1: Wettable Powders)

40 parts of a compound of the present invention, 53 parts of diatomaceous earth, 4 parts of higher alcohol sulfuric acid ester, and 3 parts of alkyl naphthalene sulfonate are mixed uniformly, and then finely pulverized to obtain wettable powders containing 40% of the active ingredient.

(Formulation 2: Emulsion)

30 parts of a compound of the present invention, 33 parts of xylene, 30 parts of dimethylformamide, and 7 parts of polyoxyethylene alkyl allyl ether are mixed and dissolved to obtain an emulsion containing 30% of the active ingredient.

(Formulation 3: Granules)

5 parts of a compound of the present invention, 40 parts of talc, 38 parts of clay, 10 parts of bentonite, and 7 parts of sodium alkyl sulfate are mixed uniformly, and then finely pulverized, followed by conducting granulation to obtain a particle diameter of 0.5 to 1.0 mm, and thus granules containing 5% of the active ingredient are obtained.

(Formulation 4: Granules)

5 parts of a compound of the present invention, 73 parts of clay, 20 parts of bentonite, 1 part of sodium dioctyl sulfosuccinate, and 1 part of potassium phosphate are mixed well and then pulverized, followed by adding water thereto, and then kneading the mixture. Then, granulation and drying are conducted to obtain granules containing 5% of the active ingredient.

(Formulation 5: Suspension)

10 parts of a compound of the present invention, 4 parts of polyoxyethylene alkyl allyl ether, 2 parts of sodium polycarboxylate, 10 parts of glycerin, 0.2 parts of xanthan gum, and 73.8 parts of water are mixed, and then wet-pulverized until the particle size becomes 3 μm or less to obtain a suspension containing 10% of the active ingredient.

Preparation formulations of ectoparasite control agents, endoparasite control agents or expellants are shown below.

(Formulation 6: Granules)

5 parts of a compound of the present invention is dissolved in an organic solvent to obtain a solution. The solution is sprayed on a mixture of 94 parts of kaolin and 1 part of white carbon, followed by evaporating the solvent under reduced pressure to obtain granules. The granules may be mixed with animal feed to be used.

(Formulation 7: Injection Agent)

0.1 to 1 part of a compound of the present invention and 99 to 99.9 parts of peanut oil are mixed uniformly, and then filter-sterilized using a sterilizing filter.

(Formulation 8: Pour-on Agent)

5 parts of a compound of the present invention, 10 parts of a myristic acid ester and 85 parts of isopropanol are mixed uniformly to obtain a pour-on agent.

(Formulation 9: Spot-on Agent)

10 to 15 parts of a compound of the present invention, 10 parts of a palmitic acid ester and 75 to 80 parts of isopropanol are mixed uniformly to obtain a spot-on agent.

(Formulation 10: Spray Agent)

1 part of a compound of the present invention, 10 parts of propylene glycol and 89 parts of isopropanol are mixed uniformly to obtain a spray agent.

The present invention is explained further specifically by showing synthesis examples below. The present invention is not limited to the following synthesis examples.

Example 1

Synthesis of pyrazin-1-ium-1-yl(4'-(trifluoromethoxy)-[1,1'-biphenyl]-4-carbonyl)amid

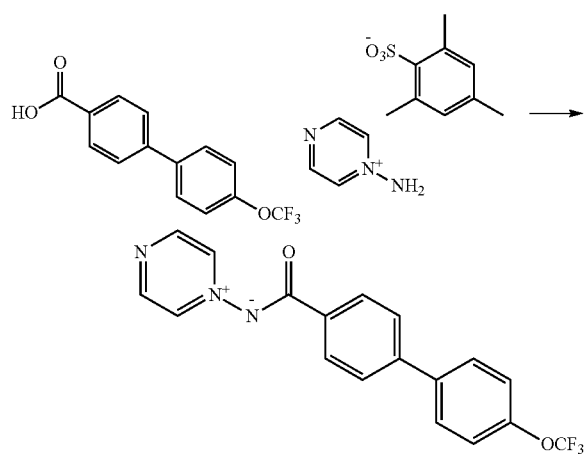

4'-(Trifluoromethoxy)-[1,1'-biphenyl]-4-carboxylic acid (71 mg) was dissolved in dichloromethane (1 ml). Oxalyl chloride (38 mg) was added to the solution, and one drop of N,N-dimethylformamide was added thereto. The resultant was stirred at room temperature for three hours. Then, the solvent was distilled off, and then dichloromethane (1 ml), 1-aminopyrazin-1-ium 2,4,6-trimethylbenzenesulfonate (81 mg) and triethylamine (61 mg) were added to the residue, followed by stirring the mixture at room temperature for 24 hours.

The resultant was condensed under reduced pressure, and then water was added to the resultant condensate, followed by collecting precipitated crystal to obtain the target product (60 mg).

Some examples of the compound of the present invention prepared in a similar manner to that of the above-mentioned example are shown in Table 1. The data of the physical property of the compound is indicated in the colomun "phsyicap property". The melting point (m.p.) is described as the physical property.

TABLE 1

| Compound number | Formula | Physical property |
|---|---|---|
| A-1 | | * |
| A-2 | | m.p. 170-172° C. |
| A-3 | | m.p. 216-218° C. |
| A-4 | | m.p. 202-204° C. |

TABLE 1-continued
| A-5 | 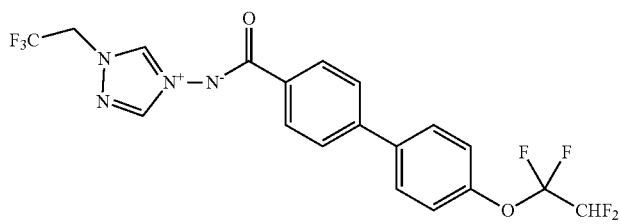 [SMILES: O=C([N-][n+]1cnn(CC(F)(F)F)c1)c1ccc(-c2ccc(OC(F)(F)C(F)F)cc2)cc1] | m.p. 227-231° C. |
| A-6 | 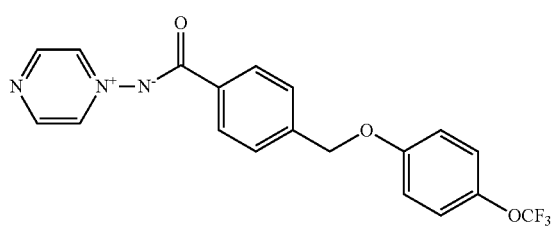 [SMILES: O=C([N-][n+]1ccncc1)c1ccc(COc2ccc(OC(F)(F)F)cc2)cc1] | m.p. 137-138° C. |
| A-7 | 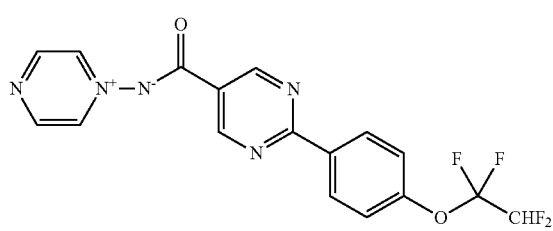 [SMILES: O=C([N-][n+]1ccncc1)c1cnc(-c2ccc(OC(F)(F)C(F)F)cc2)nc1] | m.p. 228-230° C. |
| A-8 | 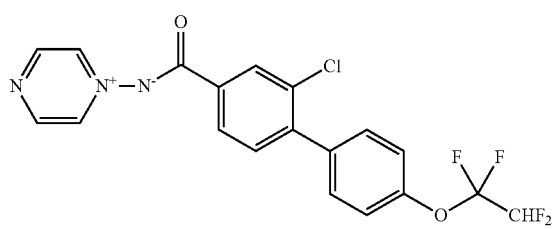 [SMILES: O=C([N-][n+]1ccncc1)c1ccc(-c2ccc(OC(F)(F)C(F)F)cc2)c(Cl)c1] | m.p. 150-152° C. |
| A-9 | 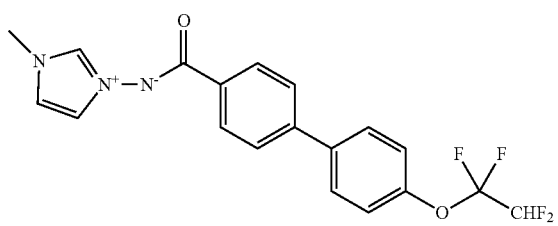 [SMILES: Cn1cc[n+]([N-]C(=O)c2ccc(-c3ccc(OC(F)(F)C(F)F)cc3)cc2)c1] | * |
| A-10 | 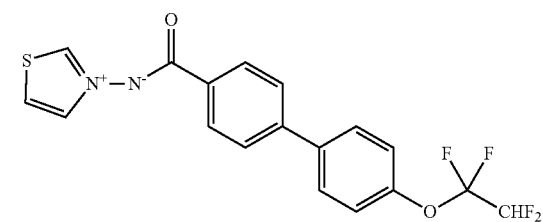 [SMILES: O=C([N-][n+]1ccsc1)c1ccc(-c2ccc(OC(F)(F)C(F)F)cc2)cc1] | m.p. 170-172° C. |
| A-11 | 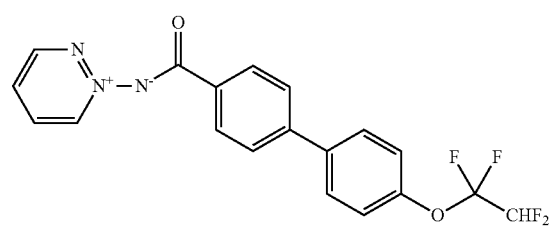 [SMILES: O=C([N-][n+]1ccccn1)c1ccc(-c2ccc(OC(F)(F)C(F)F)cc2)cc1] | m.p. 181-183° C. |

TABLE 1-continued
| | | |
|---|---|---|
| A-12 | 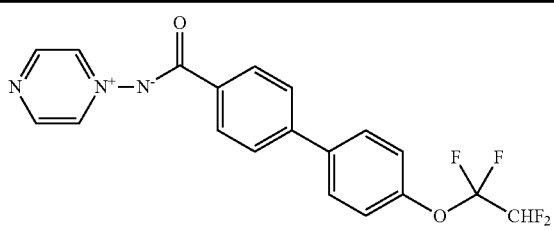 | m.p. 193-195° C. |
| A-13 | 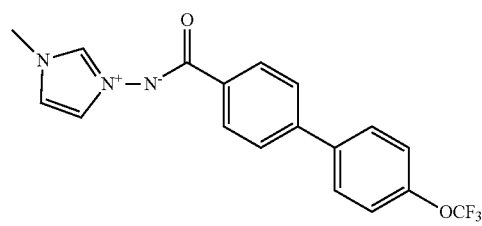 | * |
| A-14 | 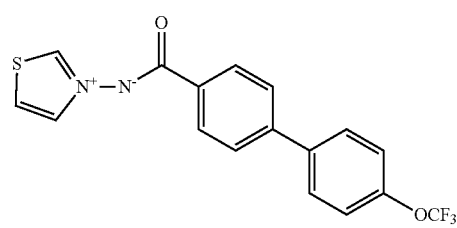 [SMILES: O=C([N-][n+]1ccsc1)c1ccc(-c2ccc(OC(F)(F)F)cc2)cc1] | m.p. 174-176° C. |
| A-15 | 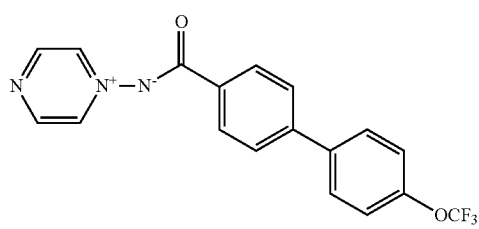 [SMILES: O=C([N-][n+]1ccncc1)c1ccc(-c2ccc(OC(F)(F)F)cc2)cc1] | m.p. 167-170° C. |
| A-16 | 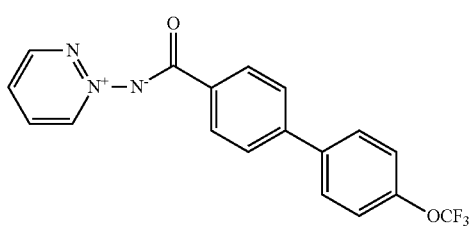 [SMILES: O=C([N-][n+]1ccccn1)c1ccc(-c2ccc(OC(F)(F)F)cc2)cc1] | m.p. 170-172° C. |
| A-17 | 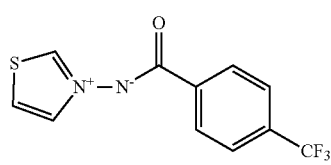 | m.p. 164-167° C. |
| A-18 | 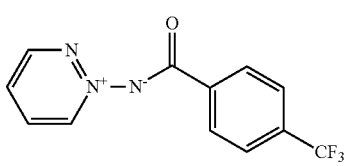 [SMILES: O=C([N-][n+]1ccccn1)c1ccc(C(F)(F)F)cc1] | m.p. 124-127° C. |
| A-19 | 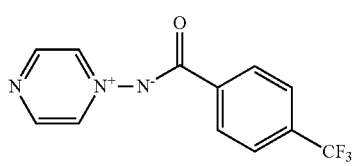 [SMILES: O=C([N-][n+]1ccncc1)c1ccc(C(F)(F)F)cc1] | m.p. 112-113° C. |

TABLE 1-continued
| A-20 | 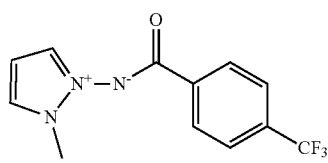 [SMILES: Cn1ccc[n+]1[N-]C(=O)c1ccc(C(F)(F)F)cc1] | m.p. 166-168° C. |
| A-21 | 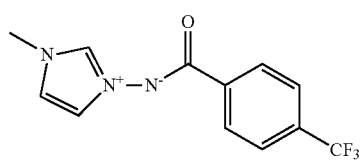 [SMILES: Cn1cc[n+]([N-]C(=O)c2ccc(C(F)(F)F)cc2)c1] | m.p. 206-207° C. |
| A-22 | 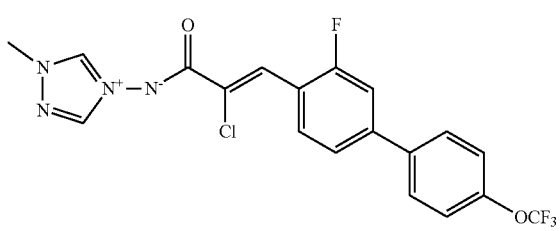 [SMILES: Cn1c[n+]([N-]C(=O)/C(Cl)=C/c2ccc(-c3ccc(OC(F)(F)F)cc3)cc2F)cn1] | m.p. 214-216° C. |
| A-23 | 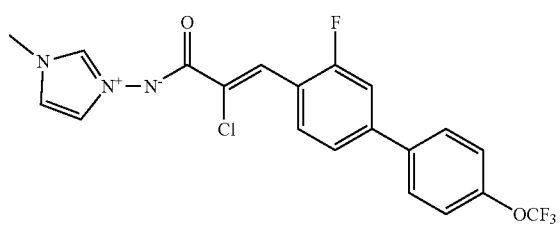 [SMILES: Cn1cc[n+]([N-]C(=O)/C(Cl)=C/c2ccc(-c3ccc(OC(F)(F)F)cc3)cc2F)c1] | m.p. 188-190° C. |
| A-24 | 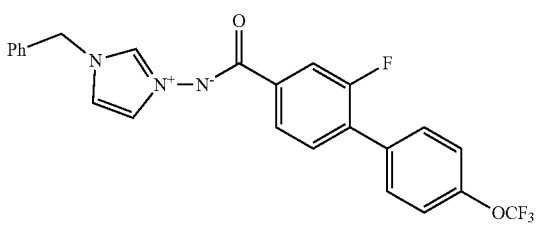 [SMILES: O=C([N-][n+]1ccn(Cc2ccccc2)c1)c1ccc(-c2ccc(OC(F)(F)F)cc2)c(F)c1] | m.p. 208-210° C. |
| A-25 | 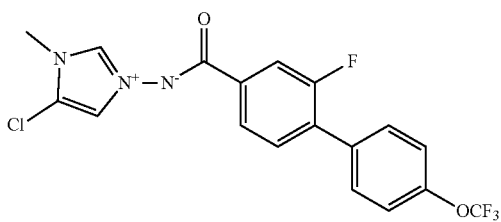 [SMILES: Cn1c[n+]([N-]C(=O)c2ccc(-c3ccc(OC(F)(F)F)cc3)c(F)c2)cc1Cl] | m.p. 246-248° C. |
| A-26 | 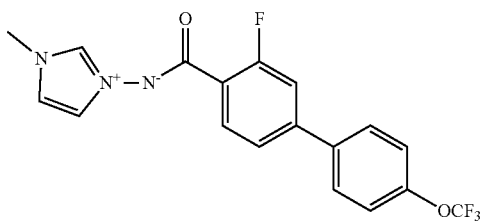 [SMILES: Cn1cc[n+]([N-]C(=O)c2ccc(-c3ccc(OC(F)(F)F)cc3)cc2F)c1] | m.p. 200-202° C. |

TABLE 1-continued
A-27 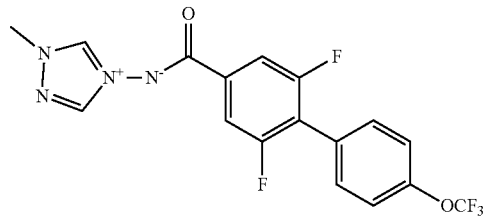 [SMILES: Cn1c[n+]([N-]C(=O)c2cc(F)c(-c3ccc(OC(F)(F)F)cc3)c(F)c2)cn1] m.p. 195-197° C.
A-28 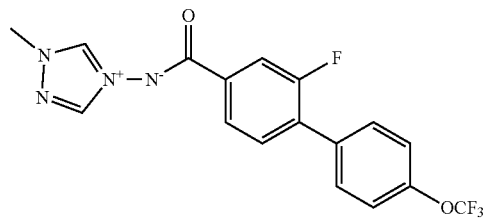 m.p. 120-122° C.
A-29 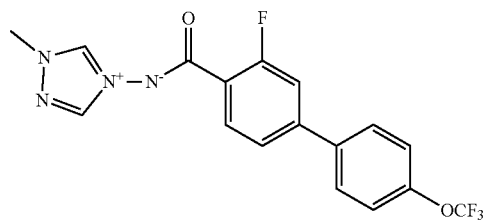 [SMILES: Cn1c[n+]([N-]C(=O)c2ccc(-c3ccc(OC(F)(F)F)cc3)cc2F)cn1] m.p. 250° C.
A-30 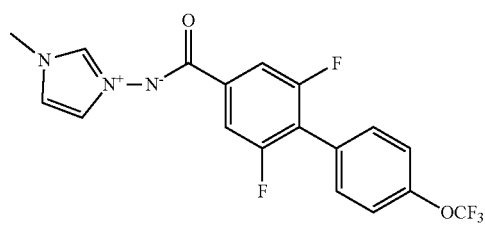 [SMILES: Cn1cc[n+]([N-]C(=O)c2cc(F)c(-c3ccc(OC(F)(F)F)cc3)c(F)c2)c1] m.p. 155-157° C.
A-31 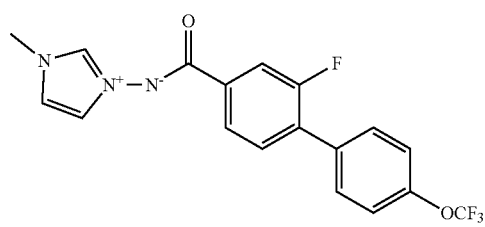 [SMILES: Cn1cc[n+]([N-]C(=O)c2ccc(-c3ccc(OC(F)(F)F)cc3)c(F)c2)c1] m.p. 157-159° C.
A-33 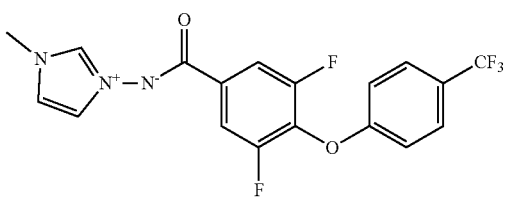 [SMILES: Cn1cc[n+]([N-]C(=O)c2cc(F)c(Oc3ccc(C(F)(F)F)cc3)c(F)c2)c1] *
A-37 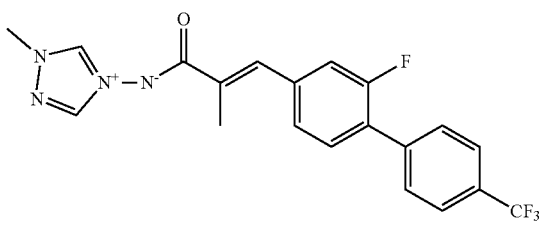 [SMILES: C/C(=C\c1ccc(-c2ccc(C(F)(F)F)cc2)c(F)c1)C(=O)[N-][n+]1cnn(C)c1] m.p. 190-192° C.

TABLE 1-continued
| A-38 | 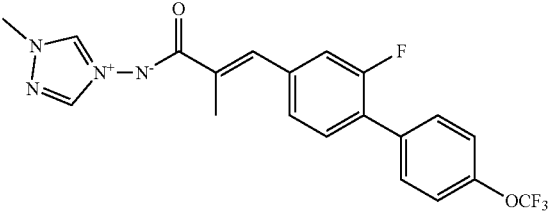 [SMILES: C/C(=C\c1ccc(-c2ccc(OC(F)(F)F)cc2)c(F)c1)C(=O)[N-][n+]1cnn(C)c1] | m.p. 167-169° C. |
| --- | --- | --- |
| A-39 | 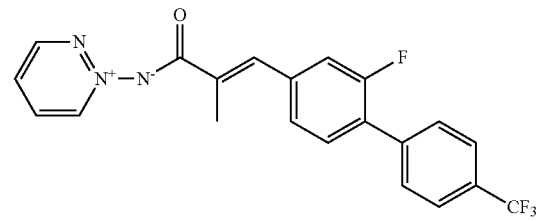 [SMILES: C/C(=C\c1ccc(-c2ccc(C(F)(F)F)cc2)c(F)c1)C(=O)[N-][n+]1ccccn1] | m.p. 156-158° C. |
| A-40 | 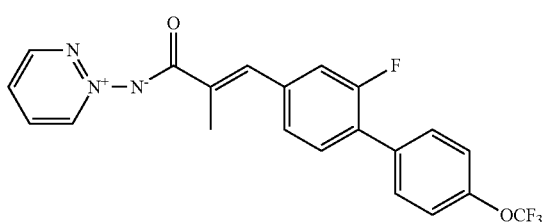 | * |
| A-41 | 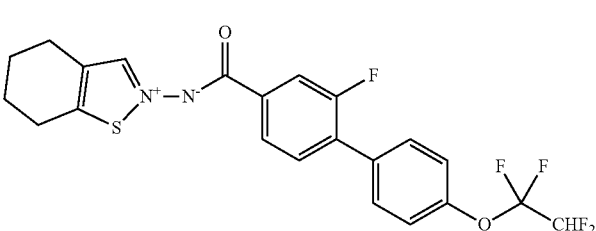 | * |
| A-42 | 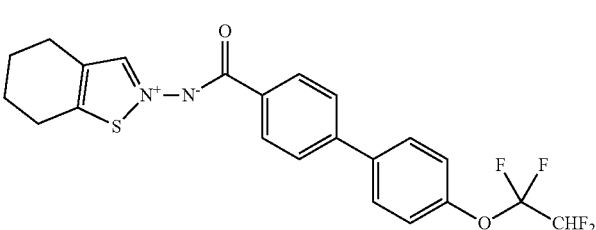 | * |
| A-43 | 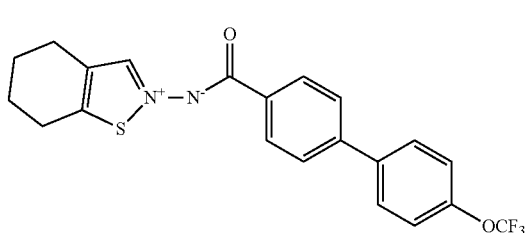 | * |
| A-44 | 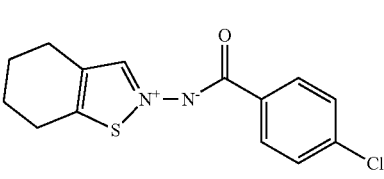 [SMILES: O=C([N-][n+]1cc2c(s1)CCCC2)c1ccc(Cl)cc1] | m.p. 161-163° C. |

TABLE 1-continued
A-46 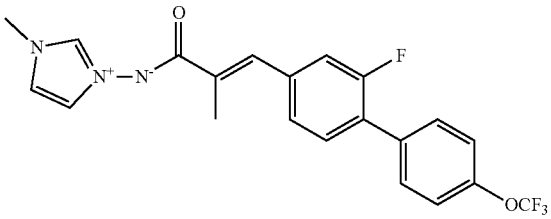 [SMILES: C/C(=C\c1ccc(-c2ccc(OC(F)(F)F)cc2)c(F)c1)C(=O)[N-][n+]1ccn(C)c1] *
A-47 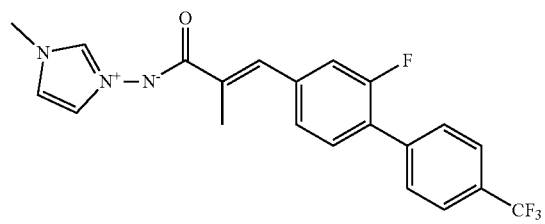 [SMILES: C/C(=C\c1ccc(-c2ccc(C(F)(F)F)cc2)c(F)c1)C(=O)[N-][n+]1ccn(C)c1] *
A-48 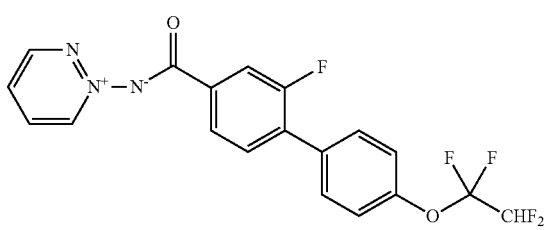 [SMILES: O=C([N-][n+]1ccccn1)c1ccc(-c2ccc(OC(F)(F)C(F)F)cc2)c(F)c1] m.p. 156-158° C.
A-49 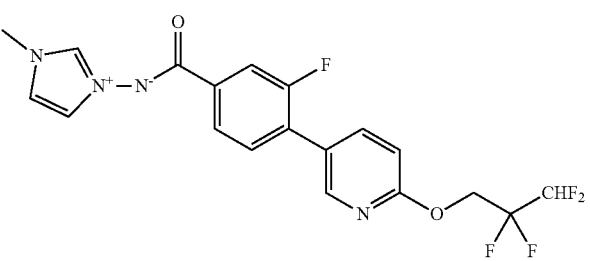 [SMILES: Cn1cc[n+]([N-]C(=O)c2ccc(-c3ccc(OCC(F)(F)C(F)F)nc3)c(F)c2)c1] m.p. 182-184° C.
A-50 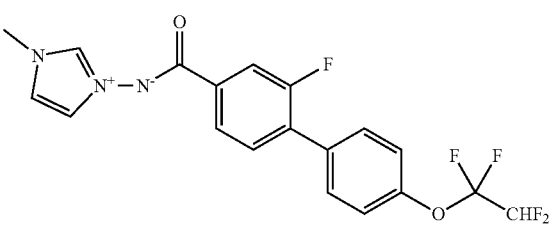 m.p. 194-195° C.
A-51 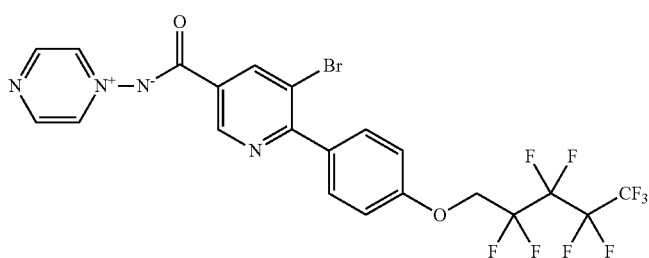 [SMILES: O=C([N-][n+]1ccncc1)c1cnc(-c2ccc(OCC(F)(F)C(F)(F)C(F)(F)C(F)(F)F)cc2)c(Br)c1] m.p. 120-122° C.

TABLE 1-continued

| | | |
|---|---|---|
| A-52 | (structure) | m.p. 184-185° C. |
| A-53 | (structure) | m.p. 194-195° C. |
| A-54 | (structure) | m.p. 219-221° C. |
| A-55 | (structure) | m.p. 182-184° C. |
| A-56 | (structure) | m.p. 167-169° C. |

| compound number | Formula | Physical property |
|---|---|---|
| A-57 | (structure) | m.p. 237-239° C. |
| A-58 | (structure) | m.p. 237-239° C. |

TABLE 1-continued

| | | |
|---|---|---|
| A-59 | (structure) | m.p. 90-93° C. |
| A-60 | (structure) | m.p. 90-93° C. |
| A-61 | (structure) | m.p. 102-103° C. |
| A-63 | (structure) | m.p. 76-79° C. |
| A-64 | (structure) | m.p. 80-83° C. |
| A-65 | (structure) | m.p. 117-118° C. |
| A-66 | (structure) | m.p. 138-140° C. |
| A-67 | (structure) | m.p. 225-256° C. |

TABLE 1-continued
A-68 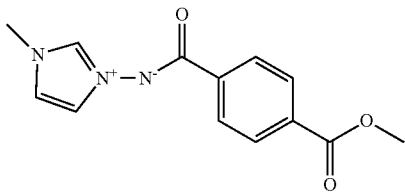 m.p. 245-246° C.
A-69 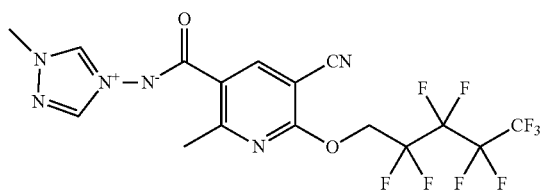 [SMILES: Cc1nc(OCC(F)(F)C(F)(F)C(F)(F)C(F)(F)F)c(C#N)cc1C(=O)[N-][n+]1cnn(C)c1] m.p. 116-118° C.
A-70 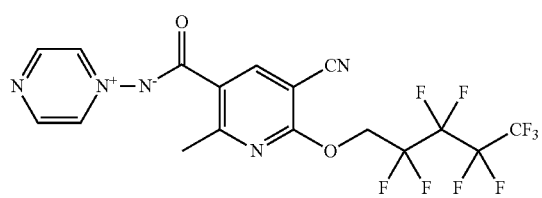 [SMILES: Cc1nc(OCC(F)(F)C(F)(F)C(F)(F)C(F)(F)F)c(C#N)cc1C(=O)[N-][n+]1ccncc1] m.p. 98-100° C.
A-71 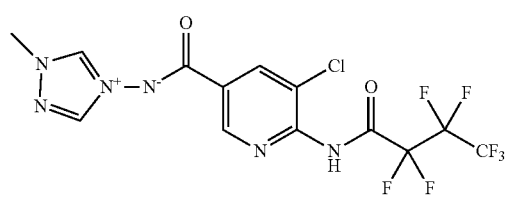 [SMILES: Cn1c[n+]([N-]C(=O)c2cnc(NC(=O)C(F)(F)C(F)(F)C(F)(F)F)c(Cl)c2)cn1] m.p. 192-194° C.
A-72 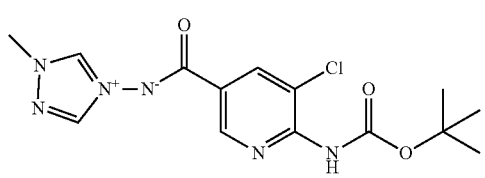 [SMILES: Cn1c[n+]([N-]C(=O)c2cnc(NC(=O)OC(C)(C)C)c(Cl)c2)cn1] m.p. 196-198° C.
A-73 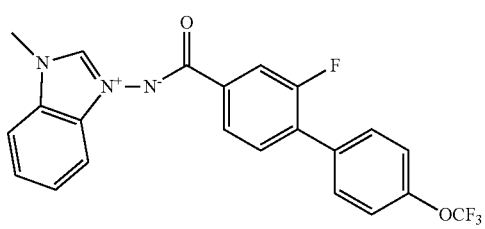 [SMILES: Cn1c[n+]([N-]C(=O)c2ccc(-c3ccc(OC(F)(F)F)cc3)c(F)c2)c2ccccc21] m.p. 180-182° C.
A-74 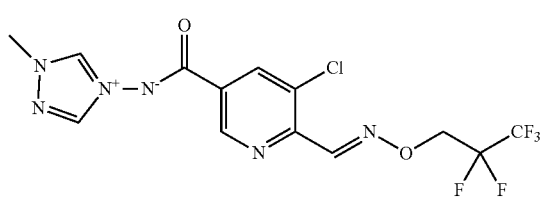 [SMILES: Cn1c[n+]([N-]C(=O)c2cnc(/C=N/OCC(F)(F)C(F)(F)F)c(Cl)c2)cn1] m.p. 194-196° C.
A-75 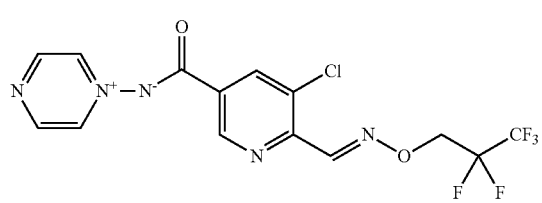 [SMILES: O=C([N-][n+]1ccncc1)c1cnc(/C=N/OCC(F)(F)C(F)(F)F)c(Cl)c1] m.p. 133-135° C.

The ¹H-NMR data of the compounds indicated by * in the column "physical property" are shown below.

Compound number (A-1): ¹H-NMR (CDCl₃) δ: 6.99-7.05 (m, 4H), 7.20 (d, 2H), 7.60 (m, 1H), 8.02 (m, 1H), 8.20 (d, 2H), 8.95 (m, 1H), 10.05 (d, 1H).

Compound number (A-9): ¹H-NMR (CDCl₃) δ: 3.91 (s, 3H), 5.92 (t, 11H), 7.10 (s, 1H), 7.27 (d, 2H), 7.50-7.54 (m, 3H), 7.59 (d, 2H), 8.12 (d, 2H), 9.64 (s, 1H).

Compound number (A-13): ¹H-NMR (CDCl₃) δ: 3.90 (s, 3H), 7.00 (s, 1H), 7.27 (m, 2H), 7.52 (s, 1H), 7.57 (d, 2H), 7.63 (d, 2H), 8.17 (d, 2H), 9.85 (s, 1H).

Compound number (A-33): ¹H-NMR (CDCl₃) δ: 3.92 (s, 3H), 6.99-7.01 (m, 3H), 7.42 (s, 1H), 7.56 (d, 2H), 7.74 (d, 2H), 9.60 (s, 1H).

Compound number (A-40): ¹H-NMR (CDCl₃) δ: 2.33 (s, 3H), 7.20-7.30 (m, 4), 7.42 (m, 1H), 7.60-7.65 (m, 3H), 7.82 (s, 1H), 8.03 (m, 1H), 8.96 (br, 1H), 10.08 (d, 1H).

Compound number (A-41): ¹H-NMR (CDCl₃) δ: 1.90-1.95 (m, 4H), 2.71 (m, 2H), 2.87 (m, 2H), 5.94 (t, 1H), 7.25-7.31 (m, 2H), 7.45 (m, 1H), 7.60-7.63 (m, 4H), 7.93 (m, 1H), 7.98 (m, 1H), 8.58 (s, 1H).

Compound number (A-42): ¹H-NMR (CDCl₃) δ: 1.90-1.95 (m, 4H), 2.70 (m, 2H), 2.85 (m, 2H), 5.94 (t, 1H), 7.24-7.30 (m, 2H), 7.61-7.68 (m, 5H), 8.20 (d, 1H), 8.59 (s, 1H).

Compound number (A-43): ¹H-NMR (CDCl₃) δ: 1.89-1.97 (m, 4H), 2.70 (m, 2H), 2.85 (m, 2H), 7.26-7.30 (m, 2H), 7.42 (m, 1H), 7.61-7.66 (m, 4H), 8.20 (m, 1H), 8.59 (s, 1H).

Compound number (A-46): ¹H-NMR (CDCl₃) δ: 2.23 (s, 3H), 3.85 (s, 3H), 6.95 (s, 1H), 7.25-7.29 (m, 4H), 7.37 (m, 1H), 7.43 (s, 1H), 7.52 (s, 1H), 7.58 (m, 2H), 9.81 (s, 1H).

Compound number (A-47): ¹H-NMR (CDCl₃) δ: 2.23 (s, 3H), 3.86 (s, 3H), 6.96 (s, 1H), 7.21-7.28 (m, 4H), 7.39-7.45 (m, 3H), 7.53 (m, 2H), 9.84 (s, 1H).

In addition, compounds of the present invention prepared in a similar manner to that of the above-mentioned example are shown in Table 2. The retention time of the compound subjected to the liquid chromatography-mass spectrometry (LCMS) is described in the column "retention time".

The retention time and the relative mass ion were measured by liquid chromatography-mass spectrometry (LCMS) using the following method.

Waters CORTECS UPLC C18 column (manufactured by Waters Corporation, 2.1×50 mm, 1.6 m) was used under the conditions in which the temperature was set at 40° C., the flow rate was set at 0.6 mL/minute, the injection amount was set at 2 μL, water containing 0.1% formic acid was used as the mobile phase (A), and acetonitrile was used as the mobile phase (B), and the retention time was count by minute.

(I) Migration was conducted using ACQUITY UPLC H-Class (manufactured by Waters Corporation) with ACQUITY UPLC photodiode array (PDA) eλ detector (manufactured by Waters Corporation) and ACQUITY QDa detector (manufactured by Waters Corporation, in which UV PDA detection was conducted in positive and negative ion electrospray modes), while increasing the concentration of the mobile phase (B) in a linear gradient from 30% by mass to 95% by mass for 1.5 minutes, (II) maintaining the concentration at 95% by mass for 0.5 minutes, (III) immediately decreasing the concentration to 30% by mass, and then (IV) maintaining the concentration at 30% by mass for 0.5 minutes.

TABLE 2

| Compound number | Formula | Retention time |
|---|---|---|
| A-76 | [structure] | 1.42 |
| A-77 | [structure] | 1.31 |
| A-78 | [structure] | 1.63 |

TABLE 2-continued

| Compound number | Formula | Retention time |
|---|---|---|
| A-79 | | 1.53 |
| A-80 | | 1.51 |
| A-81 | | 1.62 |
| A-82 | | 1.5 |
| A-83 | | 1.42 |
| A-84 | | 1.62 |
| A-85 | | 1.41 |
| A-86 | | 1.5 |

TABLE 2-continued

| Compound number | Formula | Retention time |
|---|---|---|
| A-87 | | 1.43 |
| A-88 | | 1.45 |
| A-89 | | 1.6 |
| A-90 | | 0.84 |
| A-91 | | 1.62 |
| A-92 | | 1.55 |
| A-93 | | 1.5 |
| A-94 | | 1.94 |

TABLE 2-continued
| Compound number | Formula | Retention time |
|---|---|---|
| A-95 | 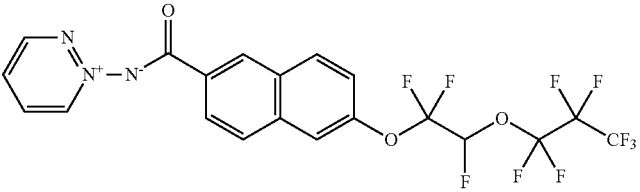 [SMILES: O=C([N-][n+]1ccccn1)c1ccc2cc(OC(F)(F)C(F)OC(F)(F)C(F)(F)C(F)(F)F)ccc2c1] | 1.56 |
| A-96 | 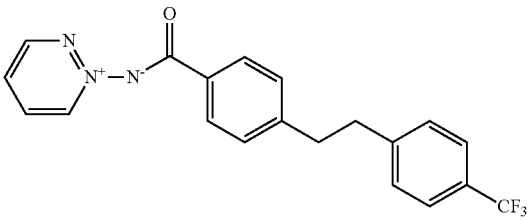 [SMILES: O=C([N-][n+]1ccccn1)c1ccc(CCc2ccc(C(F)(F)F)cc2)cc1] | 1.59 |
| A-97 | 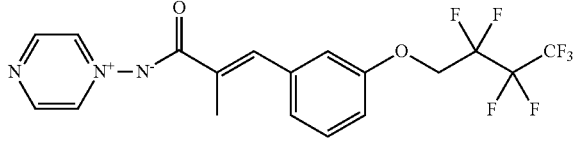 [SMILES: C/C(=C\c1cccc(OCC(F)(F)C(F)(F)C(F)(F)F)c1)C(=O)[N-][n+]1ccncc1] | 1.62 |
| A-98 | 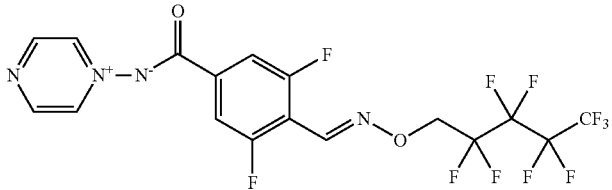 [SMILES: O=C([N-][n+]1ccncc1)c1cc(F)c(/C=N/OCC(F)(F)C(F)(F)C(F)(F)C(F)(F)F)c(F)c1] | 1.66 |
| A-99 | 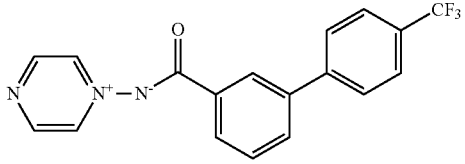 [SMILES: O=C([N-][n+]1ccncc1)c1cccc(-c2ccc(C(F)(F)F)cc2)c1] | 1.34 |
| A-100 | 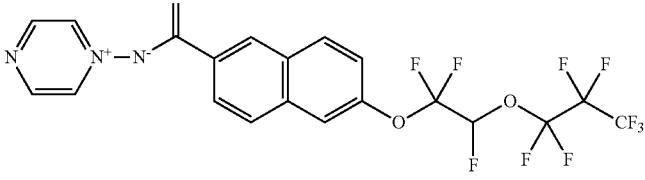 | 1.66 |
| A-101 | 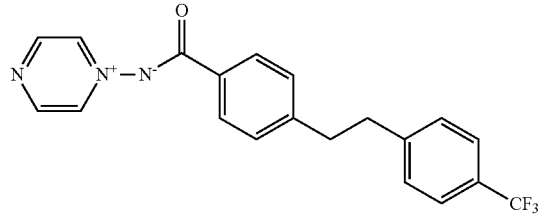 [SMILES: O=C([N-][n+]1ccncc1)c1ccc(CCc2ccc(C(F)(F)F)cc2)cc1] | 1.59 |

(Biological Test)

The following test examples show that the compound of the present invention is useful as an active ingredient of a pest control agent. The term "part" is based on the mass.

(Preparation of Test Emulsion)

5 parts by mass of a compound of the present invention, 93.6 parts by mass of dimethylformamide, and 1.4 parts by mass of polyoxyethylene alkyl aryl ether were mixed and dissolved to obtain an emulsion (I) containing 5% by mass of the active ingredient.

(Preparation of Control Emulsion)

93.6 parts by mass of dimethylformamide, and 1.4 parts by mass of polyoxyethylene alkyl aryl ether were mixed and dissolved to obtain an emulsion (II).

(1) Efficacy Test Against *Mythimna Separata*

0.8 g of commercially-available artificial feed (Insect LFS, manufactured by Nosan Corporation) and 1 µl of the emulsion (I) were mixed well, and then 0.2 g of the mixture per treated area was packed into plastic test containers (each having a capacity of 1.4 ml) as test feeds.

Two second-instar larvae of *Mythimna separata* were left per treated area, and then the test containers were sealed with plastic covers. The test containers were placed in a thermostatic chamber at 25° C., and, after five days had passed therefrom, the mortality and the feed intake were measured. The test was repeated twice.

In addition, the test was conducted under the same conditions as described above, except that the emulsion (II) was used instead of the emulsion (I), and evaluated as a solvent control area.

The compounds A-2, A-3, A-4, A-9, A-10, A-11, A-15, and A-16 were subjected to an efficacy test against *Mythimna separata*. All of the compounds caused 100% mortality of *Mythimna separata* or 10% or less of the feed intake, relative to the feed intake at the solvent control area, and thus the efficacy thereof against *Mythimna separata* was confirmed. The mortality was calculated in accordance with the following equation.

Mortality (%)=(Died insect number/Tested insect number)×100

The compounds shown in Table 3 were subjected to the efficacy test in the same way as mentioned above. All of the compounds caused 100% mortality or 10% or less of the feed intake, relative to the feed intake at the solvent control area, and thus the efficacy thereof was confirmed.

TABLE 3

| Compound number |
| --- |
| A-23 |
| A-27 |
| A-30 |
| A-31 |
| A-33 |
| A-37 |
| A-39 |
| A-40 |
| A-46 |
| A-47 |
| A-49 |
| A-51 |
| A-53 |
| A-60 |
| A-63 |
| A-64 |
| A-65 |
| A-69 |
| A-70 |
| A-76 |

TABLE 3-continued

| Compound number |
| --- |
| A-78 |
| A-79 |

(2) Efficacy Test Against *Spodoptera litura*

The emulsion (I) was diluted with water such that the amount of the compound of the present invention became 125 ppm by mass. A cabbage leaf was immersed in the diluted solution for 30 seconds. The cabbage leaf was air-dried and then put in a petri dish, followed by leaving five second-instar larvae of *Spodoptera litura* therein. The petri dish was placed in a thermostatic chamber at a temperature of 25° C. and a humidity of 60%. After six days had passed from leaving the larvae, life or death was assessed and the mortality was calculated. The test was repeated twice.

The compounds A-4, A-9, A-11 and A-13 were subjected to an efficacy test against *Spodoptera litura*. All of the compounds caused 80% or more mortality of *Spodoptera litura*.

The compounds shown in Table 4 were subjected to the efficacy test in the same way as mentioned above. All of the compounds caused at least 80% mortality.

TABLE 4

| Compound number |
| --- |
| A-23 |
| A-25 |
| A-27 |
| A-30 |
| A-31 |
| A-37 |
| A-38 |
| A-46 |
| A-47 |
| A-48 |
| A-49 |
| A-50 |
| A-52 |
| A-53 |
| A-54 |
| A-55 |
| A-56 |
| A-63 |
| A-65 |
| A-73 |

(3) Efficacy Test Against *Helicoverpa armigera*

The emulsion (I) was diluted with water such that the amount of the compound of the present invention became 125 ppm by mass. A cabbage leaf was immersed in the diluted solution for 30 seconds. The cabbage leaf was air-dried and then put in a petri dish, followed by leaving five second-instar larvae of *Spodoptera litura* therein. The petri dish was placed in a thermostatic chamber at a temperature of 25° C. and a humidity of 60%. After six days had passed from leaving the larvae, life or death was assessed and the mortality was calculated. The test was repeated twice.

The compound A-9 was subjected to an efficacy test against *Helicoverpa armigera*. The compounds caused 90% or more mortality.

(4) Efficacy Test Against *Tetranychus urticae*

Five female adults of *Tetranychus urticae* were left on primary leaves of kidney bean planted in a 3-sun pot. The emulsion (I) was diluted with water such that the amount of the compound of the present invention became 125 ppm by mass. The diluted solution was sprayed on the kidney bean and evaluated as a treated area. The 3-sun pot was placed in a thermostatic chamber at a temperature of 25° C. and a humidity of 65%, and after three days had passed from spraying, the female adults of *Tetranychus urticae* were removed to leave only laid eggs remaining on the leaves. After ten days had passed from spraying, the number of living *Tetranychus urticae* was counted. The test was repeated twice.

In addition, the test was conducted under the same conditions as described above, except that the emulsion (II) was used instead of the emulsion (I), and evaluated as a solvent control area.

The control ratio was calculated in accordance with the following equation.

Control ratio (%)=100×[1−Nt/Nc]

Nt is the living number at the treated area, and Nc is the living number at the solvent control area.

The compound A-18 was subjected to an efficacy test against *Tetranychus urticae*. The compound exhibited 90% or more control ratio.

(5) Efficacy Test Against *Aphis gossypii*

Cucumber was sown in a 3-sun pot. After ten days had passed from germination, a female adult of *Aphis gossypii* was left on the cucumber. On the next day, laid first-instar larvae were left, and the female adult was removed. The emulsion (I) was diluted with water such that the amount of the compound of the present invention became 125 ppm by mass. The diluted solution was sprayed on the cucumber. Then, the cucumber was placed in a thermostatic chamber at a temperature of 25° C. and a humidity of 60%. After five days had passed therefrom, life or death of *Aphis gossypii* was assessed and the mortality was calculated.

The compound A-19 was subjected to an efficacy test against *Aphis gossypii*. The compound caused 80% or more mortality.

(6) Efficacy Test Against *Nilaparvata lugens*

The emulsion (I) was diluted with water such that the amount of the compound of the present invention became 125 ppm by mass. A rice seedling was immersed in the diluted solution for 30 seconds, air-dried, and then placed in a plastic case, followed by leaving five second-instar larvae of *Nilaparvata lugens* therein. The plastic case was placed in a thermostatic chamber at a temperature of 25° C. and a humidity of 65%. After ten days had passed therefrom, life or death was assessed and the mortality was calculated. The test was repeated twice.

The compound A-11 was subjected to an efficacy test against *Nilaparvata lugens*. The compound caused 80% or more mortality.

(7) Efficacy Test Against *Tetranychus kanzawai*

Five female adults of *Tetranychus kanzawai* were left on primary leaves of mung bean planted in a 3-sun pot. The emulsion (I) was diluted with water such that the amount of the compound of the present invention became 125 ppm by mass. The diluted solution was sprayed on the mung bean and evaluated as a treated area. In addition, the test was conducted under the same conditions as described above, except that the compound of the present invention was removed from the emulsion (1), and evaluated as a solvent control area. The 3-sun pot was placed in a thermostatic chamber at a temperature of 25° C. and a humidity of 65%, and after four days had passed from spraying, the female adults of *Tetranychus kanzawai* were removed to leave only laid eggs remaining on the leaves. After eleven days had passed from spraying, the number of living *Tetranychus kanzawai* was counted and the control ratio was calculated in accordance with the above-mentioned equation. The test was repeated twice.

The compounds A-23, A-37, A-47, A-48, A-49, and A-50 were subjected to an efficacy test against *Tetranychus kanzawai*. All of the compounds exhibited 90% or more control ratio.

Since the compounds randomly selected from the aromacyclic quaternary ammonium compounds of the present invention exhibited the above-described effects, it is understood that the aromacyclic quaternary ammonium compound of the present invention, involving aspects of the compound that are not shown in the above examples, is a compound that exhibits pest control effects, acaricidal effects, and particularly insecticidal effects.

INDUSTRIAL APPLICABILITY

The aromacyclic quaternary ammonium compound of the present invention has control activity against pests that cause problems to agricultural crops or in the health field. The control agent containing the aromacyclic quaternary ammonium compound of the present invention can effectively control pests, particularly agricultural insect pests and acarians, at lower doses, and can further effectively control ectoparasites and endoparasites that may harm humans and animals.

The invention claimed is:
1. A compound of formula (I) or formula (II):

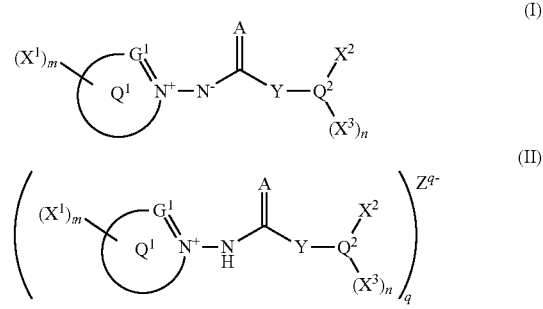

wherein, in the formulae (I) and (II),
  $Q^1$ is a pyrazole ring, an imidazole ring, a 1,2,4-triazole ring, an oxazole ring, an isoxazole ring, a pyrazine ring, a pyrimidine ring, or a pyridazine ring,
  $G^1$ is a nitrogen atom or a carbon atom,
  $X^1$ is a halogeno group, a substituted or unsubstituted C1-6 alkyl group, a substituted or unsubstituted C2-6 alkenyl group, a substituted or unsubstituted C2-6 alkynyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- or 6-membered heteroaryl group, a pentafluorosulfanyl group, a nitro group, or a cyano group,
  m indicates a number of $X^1$, and is an integer of 1 to 3 when $Q^1$ is a pyrazole ring, an imidazole ring, or a 1,2,4-triazole ring, and is an integer of 0 to 3 when Q¹ is an oxazole ring, an isoxazole ring, a pyrazine ring, a pyrimidine ring, or a pyridazine ring, X¹ on adjacent carbon atoms may form together a cyclohexene ring including the two carbon atoms, A is an oxygen atom or a sulfur atom, Y is a single bond, or a substituted or unsubstituted C2-6 alkenylene group, Q² is a benzene ring, a naphthalene ring, or a 5- to 10-membered heteroaryl ring, X² is a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C3-8 cycloalkyloxy group, a substituted or unsubstituted C6-10 aryl group, a substituted or unsubstituted C6-10 aryloxy group, a substituted or unsubstituted 5- or 6-membered heteroaryl group, a substituted or unsubstituted 5- or 6-membered heteroaryloxy group, a formyl group, a group of R—CO—, a group of RO—CO—, an amino group, a group of RNH—, a group of $R_2$N—, a group of RCONH—, a group of RO—CONH—, a carbamoyl group, a group of RNH—CO—, a group of $R_2$N—CO—, a group of RO—N=CH—, a pentafluorosulfanyl group, a nitro group, or a cyano group, R is each independently a substituted or unsubstituted C1-6 alkyl group, a substituted or unsubstituted C6-10 aryl group, or a substituted or unsubstituted 5- or 6-membered heteroaryl group, X³ is a halogeno group, a substituted or unsubstituted C1-6 alkyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a nitro group, or cyano group, n indicates a number of X³, and n is an integer of 0 to 4, when Q² is a benzene ring, and is an integer of 0 to 3, when Q² is a 5- or 6-membered heteroaryl ring, X² and X³ on adjacent carbon atoms may form together a substituted or unsubstituted 5-membered hetero ring including the two carbon atoms, $Z^{q-}$ is a counter ion, and q indicates a valence of the counter ion and is 1 or 2.

2. A pest control agent comprising at least one compound of formula (I) or formula (II) of claim 1.

3. An insecticide or acaricide comprising at least one compound of formula (I) or formula (II) of claim 1.

4. An ectoparasite control agent comprising at least one compound of formula (I) or formula (II) of claim 1.

5. An endoparasite control agent or expellant comprising at least one compound of formula (I) or formula (II) of claim 1.

6. A compound of formula (I):

$$(X^1)_m \overset{G^1}{\underset{Q^1}{\bigcirc}} \overset{A}{\underset{N^+-N^-}{\parallel}} \overset{X^2}{\underset{Y-Q^2}{\diagdown}} (X^3)_n \quad (1)$$

wherein, in the formula (I),

Q¹ is an imidazole ring, a 1,2,4-triazole ring, a pyrazine ring, or a pyridazine ring, G¹ is a nitrogen atom or a carbon atom, X¹ is a halogeno-substituted or unsubstituted C1-6 alkyl group, m indicates a number of X¹, and is an integer of 1 to 3 when Q¹ is an imidazole ring, or a 1,2,4-triazole ring, and is an integer of 0 to 3 when Q¹ is pyrazine ring, or a pyridazine ring, X¹ on adjacent carbon atoms may form together a cyclohexene ring including the two carbon atoms, A is an oxygen atom, Y is a single bond, or a halogeno-substituted or C1-6 alkyl-substituted C2-6 alkenylene group, Q² is a benzene ring, or a pyridine ring, X² is a substituted C1-6 alkyl group, a substituted C1-6 alkoxy group, a substituted phenyl group, a substituted phenoxy group, or a substituted pyridyl group, a substituent on the substituted C1-6 alkyl group or C1-6 alkoxy group being a halogeno group or a C1-6 haloalkoxy group, a substituent on the substituted phenyl group, phenoxy group, or pyridyl group being a C1-6 haloalkyl group or a C1-6 haloalkoxy group, X³ is a halogeno group, an unsubstituted C1-6 alkyl group, or cyano group, n indicates a number of X³, and n is an integer of 0 to 4, when Q² is a benzene ring, and is an integer of 0 to 3, when Q² is the pyridine ring.

7. A pest control agent comprising at least one compound of formula (I) of claim 6.

8. An insecticide or acaricide comprising at least one compound of formula (I) of claim 6.

9. An ectoparasite control agent comprising at least one compound of formula (I) of claim 6.

10. An endoparasite control agent or expellant comprising at least one compound of formula (I) of claim 6.

* * * * *